(12) United States Patent
Takahashi et al.

(10) Patent No.: US 10,357,203 B2
(45) Date of Patent: Jul. 23, 2019

(54) BIOLOGICAL INFORMATION DETECTION DEVICE

(71) Applicant: Seiko Epson Corporation, Tokyo (JP)

(72) Inventors: Yusuke Takahashi, Matsumoto (JP); Ichiro Aoshima, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 535 days.

(21) Appl. No.: 14/990,714

(22) Filed: Jan. 7, 2016

(65) Prior Publication Data

US 2016/0113588 A1 Apr. 28, 2016

Related U.S. Application Data

(63) Continuation of application No. PCT/JP2014/003651, filed on Jul. 9, 2014.

(30) Foreign Application Priority Data

Jul. 12, 2013 (JP) .................................. 2013-146449
Jul. 12, 2013 (JP) .................................. 2013-146450

(51) Int. Cl.
*A61B 5/00* (2006.01)
*A61B 5/024* (2006.01)

(52) U.S. Cl.
CPC ........ *A61B 5/7221* (2013.01); *A61B 5/02416* (2013.01); *A61B 5/02438* (2013.01); *A61B 5/681* (2013.01); *A61B 5/6824* (2013.01); *A61B 5/721* (2013.01)

(58) Field of Classification Search
None
See application file for complete search history.

(56) References Cited

U.S. PATENT DOCUMENTS

| 4,644,479 A | * | 2/1987 | Kemper | ............ | G05B 23/0278 |
| | | | | | 700/79 |
| 6,035,223 A | * | 3/2000 | Baker, Jr. | ............ | A61B 5/0059 |
| | | | | | 600/300 |
| 6,099,478 A | | 8/2000 | Aoshima et al. | | |
| 6,475,153 B1 | * | 11/2002 | Khair | ................ | A61B 5/02007 |
| | | | | | 600/485 |

(Continued)

FOREIGN PATENT DOCUMENTS

| JP | H10-019766 A | 1/1998 |
| JP | H10-258040 A | 9/1998 |

(Continued)

*Primary Examiner* — Michael R Bloch
(74) *Attorney, Agent, or Firm* — Kilpatrick Townsend & Stockton LLP

(57) ABSTRACT

A biological information detection device or the like which can determine a mounted state or an unmounted state with high accuracy, or can appropriately present information on the basis of a determination result is to be provided.
A biological information detection device includes a pulse wave detection unit 10 that outputs a pulse wave sensor signal and a processing unit 100 that processes the pulse wave sensor signal, in which the processing unit 100 performs a detachment detection process of the biological information detection device on the basis of a DC component change value of the pulse wave sensor signal in a predetermined period.

5 Claims, 21 Drawing Sheets

(56) References Cited

U.S. PATENT DOCUMENTS

| | | | | |
|---|---|---|---|---|
| 6,526,300 B1* | 2/2003 | Kiani | ............... | A61B 5/14552 |
| | | | | 600/322 |
| 6,608,562 B1* | 8/2003 | Kimura | ............. | A61B 5/02427 |
| | | | | 128/903 |
| 6,654,624 B2* | 11/2003 | Diab | ................. | A61B 5/14551 |
| | | | | 600/336 |
| 2002/0137995 A1* | 9/2002 | Heckel | ............... | A61B 5/14551 |
| | | | | 600/323 |
| 2009/0182239 A1 | 7/2009 | Ouchi et al. | | |
| 2012/0215115 A1 | 8/2012 | Takahashi | | |
| 2014/0176944 A1* | 6/2014 | Addison | ............... | G01B 11/14 |
| | | | | 356/400 |
| 2015/0065892 A1 | 3/2015 | Ouchi et al. | | |

FOREIGN PATENT DOCUMENTS

| | | |
|---|---|---|
| JP | 2001-070266 A | 3/2001 |
| JP | 2005-270544 A | 10/2005 |
| JP | 2009-153832 A | 7/2009 |
| JP | 2012-170702 A | 9/2012 |

\* cited by examiner

| | CURRENT STATE | DESCRIPTION | EVENT ID | EVENT NAME | EVENT DETERMINATION CONTENT | STATE TRANSITION DESTINATION |
|---|---|---|---|---|---|---|
| A | PULSE MEASUREMENT UNSUCCESSFUL STATE | MEASUREMENT START BUTTON IS PRESSED, BUT PULSE RATE IS NOT DISPLAYED | A1 | INITIAL PULSE MEASUREMENT SUCCESSFUL EVENT | HAS PULSE BEEN MEASURED? | B |
| | | | A2 | UNSUCCESSFUL MEASUREMENT LASTING EVENT FOR SPECIFIC TIME | DOES STATE A LAST FOR SPECIFIC TIME OR MORE? | F |
| B | MOUNTED STATE (RELIABLE) | PULSE RATE CAN BE DISPLAYED WITHOUT DETACHING DEVICE FROM ARM | B1 | DETACHMENT EVENT | HAS ABNORMALITY OCCURRED IN ∆PULSE DC AND HAS IMPACT NOT BEEN DETECTED? | D |
| | | | B2 | IMPACT OCCURRENCE EVENT | HAS ABNORMALITY OCCURRED IN ∆PULSE DC AND HAS IMPACT BEEN DETECTED? | C |
| C | MOUNTED STATE (DOUBTFUL) | ABNORMALITY IS OBSERVED IN PULSE DC BUT DEVICE IS MOUNTED | C1 | DETACHMENT EVENT | HAS ABNORMALITY OCCURRED IN ∆PULSE DC AND HAS IMPACT NOT BEEN DETECTED? | D |
| | | | C2 | IMPACT END EVENT | HAS IMPACT NOT BEEN DETECTED FOR SPECIFIC TIME AND HAS ABNORMALITY NOT OCCURRED IN ∆PULSE DC? | B |
| D | UNMOUNTED STATE (RELIABLE) | DEVICE IS DETACHED FROM ARM | D1 | MOUNTING DETECTION EVENT | HAS ABNORMALITY WHICH IS EQUAL TO OR GREATER THAN ∆PULSE DC LONGITUDE, HAS PULSE DC SHIFTED, AND HAS SUBSEQUENT PULSE DC BEEN STABILIZED? (AND, OPTIONALLY, IS WAVEFORM OF PULSE AC FINE?) | E |
| | | | D2 | UNMOUNTED STATE LASTING EVENT FOR SPECIFIC TIME | DOES STATE D LAST FOR SPECIFIC TIME OR MORE? | F |
| E | UNMOUNTED STATE (DOUBTFUL) | THERE IS POSSIBILITY THAT PULSIMETER MAY BE REMOUNTED SINCE CHANGE IN PULSE DC IS OBSERVED | E1 | EXTERNAL LIGHT DETECTION EVENT | DOES VALUE OF PULSE DC INDICATE LIGHT INTENSITY WHICH IS NOT EXPECTED IN MOUNTED STATE? | D |
| | | | E2 | MIDDLE PULSE MEASUREMENT SUCCESSFUL EVENT | IS THERE NO ABNORMALITY IN ?PULSE DC, IS VALUE OF PULSE DC WITHIN MOUNTING RANGE, IS WAVEFORM OF PULSE AC FINE, AND HAS MEASUREMENT OF PULSE BEEN SUCCESSFUL? | B |
| F | MEASUREMENT FINISH STATE | STATE IN WHICH MEASUREMENT IS FINISHED SINCE UNMOUNTED STATE LASTS FOR A LONG PERIOD OF TIME | — | — | — | — |

N INDICATES NO OCCURRENCE OF EVENT

FIG. 14

| EVENT ASSOCIATED PROCESS | | SCREEN | | | | | | | SPREADING PROCESS | | | | | STATE TRANSITION DESTINATION |
|---|---|---|---|---|---|---|---|---|---|---|---|---|---|---|
| EVENT ID | EVENT NAME | MAIN DISPLAY | ICON DISPLAY TYPE | PULSE RATE | SENSING SENSITIVITY | SCREEN DECORATION | SOUND | VIBRATION | NOISE FILTER | PULSE DETERMINATION PROCESS | NUMBER OF STEPS, CALORIES | PULSE SENSOR LED | DATA TRANSMISSION CONTENT | |
| S1 | MEASUREMENT BUTTON PRESSING EVENT | – | – | – | – | – | – | – | INITIALIZE | INITIALIZE | INITIALIZE | – | NOTIFY OF STARTING USE OF DEVICE | A |
| A1 | INITIAL PULSE MEASUREMENT SUCCESSFUL EVENT | – | – | – | – | LIGHTING FOR ONE SECOND | SHORT | ONCE | – | – | – | – | TRANSMIT CONTENT THAT MEASUREMENT IS SUCCESSFUL | B |
| A2 | MEASUREMENT UNSUCCESSFUL STATE LASTING EVENT FOR SPECIFIC TIME | – | – | – | – | BLINKING FOR TEN SECONDS | – | – | – | – | – | – | – | F |
| B1 | DETACHMENT EVENT | – | BLINKING FOR FOUR SECONDS | – | – | BLINKING FOR FOUR SECONDS | LONG | THREE TIMES | – | – | – | – | OCCURRENCE OF DETACHMENT OF DEVICE | D |
| B2 | IMPACT OCCURRENCE EVENT | – | BLINKING FOR FOUR SECONDS | – | – | – | – | – | – | – | – | – | – | C |
| C1 | DETACHMENT EVENT | – | – | – | – | – | – | – | – | – | – | – | OCCURRENCE OF DETACHMENT OF DEVICE | D |
| C2 | IMPACT END EVENT | – | – | – | – | – | – | – | – | – | – | – | – | B |
| D1 | MOUNTING DETECTION EVENT | – | – | – | – | – | – | – | INITIALIZE | INITIALIZE | – | – | – | E |
| D2 | UNMOUNTED STATE LASTING EVENT FOR SPECIFIC TIME | – | – | – | – | BLINKING FOR TEN SECONDS | – | – | – | – | – | – | – | F |
| E1 | EXTERNAL LIGHT DETECTION EVENT | – | – | – | – | – | – | – | – | – | – | – | NOTIFY THAT MEASUREMENT IS SUCCESSFUL (REMOUNTING) | D |
| E2 | MIDDLE PULSE MEASUREMENT SUCCESSFUL EVENT | – | – | – | – | LIGHTING FOR ONE SECOND | SHORT | ONCE | – | – | – | – | – | B |
| N | NO OCCURRENCE OF EVENT | – | – | – | – | – | – | – | – | – | – | – | – | NO |

FIG. 20A

| STATE ASSOCIATED PROCESS | | SCREEN | | | | | | | SPREADING PROCESS | | | | |
|---|---|---|---|---|---|---|---|---|---|---|---|---|---|
| STATE ID | STATE NAME | MAIN DISPLAY | ICON DISPLAY TYPE | PULSE RATE | SENSING SENSITIVITY | SCREEN DECORATION | SOUND | VIBRATION | NOISE FILTER | PULSE DETERMINATION PROCESS | NUMBER OF STEPS, CALORIES | PULSE SENSOR LED | DATA TRANSMISSION CONTENT |
| S | STANDBY STATE (CLOCK DISPLAY OR THE LIKE) | CLOCK | NO DISPLAY | NO DISPLAY | NO DISPLAY | NO LIGHTING | — | — | — | — | — | TURNING OFF | — |
| A | PULSE MEASUREMENT UNSUCCESSFUL STATE | DURING MEASUREMENT | ◇ | — | ▶≡ (BLINKING) | LIGHT BLUE | — | — | EXECUTE | EXECUTE (STRICT DETERMINATION) | — | LIGHTING | — |
| B | MOUNTED STATE (RELIABLE) | DURING MEASUREMENT | ▶ | NUMERICAL VALUE | ▶≡ | WHITE | — | — | EXECUTE | EXECUTE | — | LIGHTING | — |
| C | MOUNTED STATE (DOUBTFUL) | DURING MEASUREMENT | ? | NUMERICAL VALUE (BLINKING) | ▶∣ | YELLOW | — | — | EXECUTE | EXECUTE (STRICT DETERMINATION) | — | LIGHTING | — |
| D | UNMOUNTED STATE (RELIABLE) | DURING MEASUREMENT | △ | — | ▶ | RED | — | INTERVAL OF ONE SECOND | TEMPORARILY STOP | TEMPORARILY STOP | STOP ACCUMULATION | TURNING OFF OR LOW-CURRENT LIGHTING | TRANSMIT CONTENT OF BEING IN TEMPORARY STOPPAGE STATE |
| E | UNMOUNTED STATE (DOUBTFUL) | DURING MEASUREMENT | △ | — | ▶ | RED | — | INTERVAL OF ONE SECOND | — | — | STOP ACCUMULATION | LIGHTING | TRANSMIT CONTENT OF BEING IN TEMPORARY STOPPAGE STATE |
| F | MEASUREMENT FINISH STATE | MEASUREMENT FINISH | NO DISPLAY | MINIMUM, MAXIMUM, AVERAGE | NO DISPLAY | NO LIGHTING | — | — | FINISH | FINISH | FINISH | TURNING OFF | TRANSMIT MEASURED DATA |

FIG. 20B

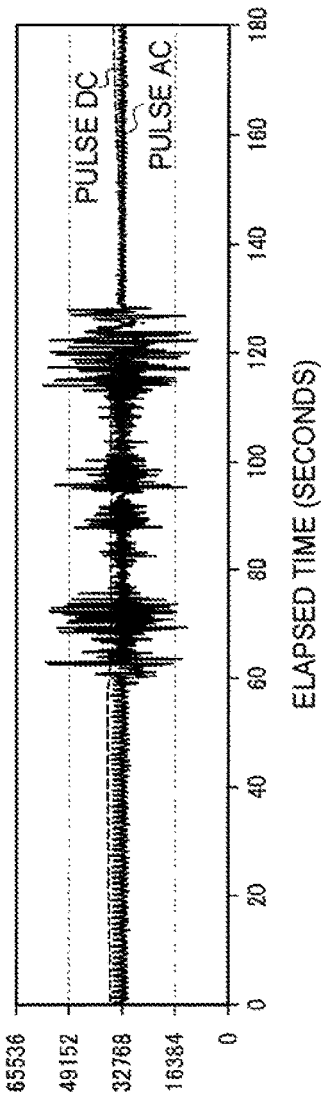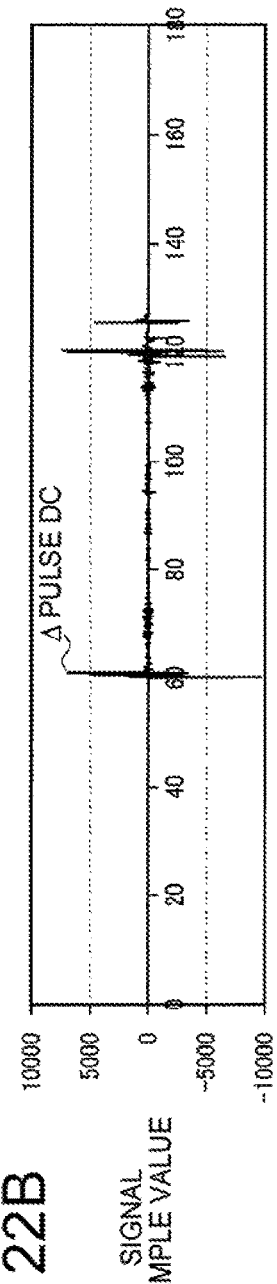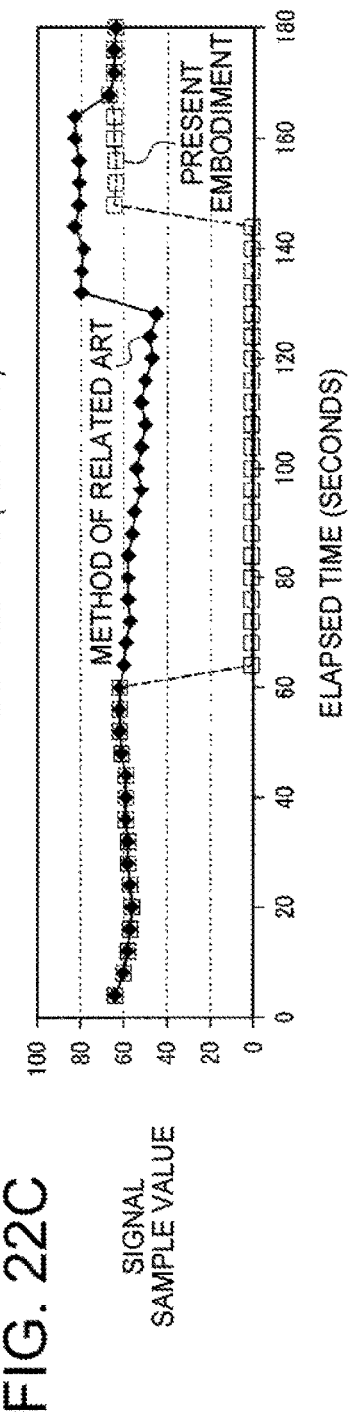

BIOLOGICAL INFORMATION DETECTION DEVICE

CROSS-REFERENCES TO RELATED APPLICATIONS

This application is a continuation of claims PCT Application PCT/JP2014/003651, filed Jul. 9, 2014, which claims priority to Japanese Patent Applications Nos. 2013-146449, filed Jul. 12, 2013, and 2013-146450, filed Jul. 12, 2013, the entireties of which are hereby incorporated by reference.

BACKGROUND

Technical Field

The present invention relates to a biological information detection device or the like.

Background Art

In recent years, a biological information detection device which is mounted on a user's arm or the like and is used has been widespread. Biological information detected by the biological information detection device may include, for example, pulse wave information such as a pulse rate. The biological information detection device in this case is a pulsimeter in a narrow sense, and performs measurement or the like of a pulse rate of the user on the basis of a signal from a pulse wave sensor included in the pulsimeter.

In a biological information detection device mounted on the arm or the like, whether or not the biological information detection device is in a mounted state or an unmounted state is important information. For example, a case is assumed in which a pulse wave sensor includes a light emitting portion (an LED or the like) and a light receiving portion (a photodiode or the like), and the light receiving portion detects reflected light which is obtained as a result of light from the light emitting portion being reflected at a living body, or transmitted light which is transmitted through the living body. In this case, light to be detected by the light receiving portion is the reflected light or the transmitted light. If the biological information detection device is in a mounted state, the reflected light or the transmitted light can be detected, but, in an unmounted state, a relative positional relationship between the pulse wave sensor and the living body is not fixed, and thus the reflected light or the transmitted light cannot be appropriately detected.

In addition, in the unmounted state, there is a high possibility that the light receiving portion may detect external light such as ambient light, and, in this case, the pulse wave sensor outputs a signal value having no relation to a user's pulse. If the signal value having no relation to the pulse is wrongly recognized as a pulse wave signal, a calculated pulse rate or the like does not reflect a user's pulse state, and thus this also exerts an adverse effect on a process (for example, an advice process regarding a health state of a target user) using the pulse rate or the like.

If a mounted state of the biological information detection device is input by a user every time, the mounted state can be detected with high accuracy. However, such an operation is cumbersome, and thus there is an increasing demand for automatically determining a mounted state of the biological information detection device from the viewpoint of convenience of use.

For example, PTL 1 discloses that an output voltage value of a pulse wave sensor differs in a mounted state and an unmounted state. Therefore, a mounted state or an unmounted state may be determined by comparing a voltage value of the pulse wave sensor with a predetermined threshold value.

CITATION LIST

Patent Literature

PTL 1: JP-A-2005-270544

SUMMARY OF INVENTION

Technical Problem

An output voltage value of the pulse wave sensor changes depending on various factors. For example, a voltage value of the pulse wave sensor differs in a case where a user stays outdoors in fine weather in which an influence of external light is great and a case where the user stays in a dark room. Alternatively, although an amount of hemoglobin or melanin in the user's skin has an individual difference, a voltage value of the pulse wave sensor changes due to a difference between attenuation rates of LED light caused by such a difference between these amounts. In addition, in the biological information detection device, it is also known that a voltage value of the pulse wave sensor changes due to pressing indicating pressure of a pulse wave sensor portion relative to a living body (skin).

Therefore, simple comparison between an output voltage value of the pulse wave sensor and a predetermined threshold value does not handle the change in a voltage value caused by the factors, and may cause a concern that a mounted state and an unmounted state may be wrongly determined.

In addition, even if a mounted state or an unmounted state can be determined with high accuracy, a method of switching processes between recording and communication of acquired biological information (pulse wave information in a narrow sense) on the basis of a determination result is not disclosed in methods of the related art.

This is because since a biological information detection device mounted on the arm or the like is required to be small and lightweight, there is a restriction in battery capacity or the like in most cases, and thus continuous usage thereof for a long period of time is not expected. Therefore, when pulse wave information is measured, since it is expected that a user wears the biological information detection device with a clear intention, there is a low necessity for taking into consideration a danger in which an inappropriate signal is detected in an unmounted state, and pulse wave information is calculated on the basis of the signal.

However, the present applicant implements a biological information detection device which can perform continuous operations for a long period of time while realizing a small size and a light weight by taking into consideration a structure of the biological information detection device including a pulse wave sensor, content of a calculation process of pulse wave information based on a pulse wave sensor signal, or the like. In this case, the biological information detection device does not detect biological information only in a specific situation (for example, during exercise) but detects for a long period of time (a day in a narrow sense) including business time or sleeping time, and can use the biological information as a "life log".

In detection of the life log, since a user is not forced to wear the biological information detection device for 24 hours in 365 days, a lot of situations may occur in which the biological information detection device is in an unmounted state while measuring a pulse wave sensor signal. In this case, if appropriate pulse wave information which is acquired in a mounted state and inappropriate pulse wave information which is acquired in an unmounted state are treated in an equivalent manner, this causes problems in processes using the pulse wave information.

According to some aspects of the invention, it is possible to provide a biological information detection device or the like which can determine a mounted state and an unmounted state with high accuracy and can appropriately present information on the basis of a determination result.

In addition, according to some aspects of the invention, it is possible to provide a biological information detection device which determines a mounted state and an unmounted state with high accuracy by using a change value of a DC component of a pulse wave sensor signal during a predetermined period.

Further, according to some aspects of the invention, it is possible to provide a biological information detection device which can perform an appropriate process based on pulse wave information by switching a process of recording or communication of the pulse wave information in a case of an unmounted state compared with a case of a mounted state.

Still further, according to some aspects of the invention, it is possible to provide a biological information detection device which can perform appropriate presentation of pulse wave information by switching a display process of the pulse wave information in a case of an unmounted state compared with a case of a mounted state.

Solution to Problem

According to an aspect of the invention, there is provided a biological information detection device including a pulse wave detection unit that outputs a pulse wave sensor signal; and a processing unit that processes the pulse wave sensor, in which the processing unit performs a detachment detection process of the biological information detection device on the basis of a DC component change value of the pulse wave sensor signal in a predetermined period.

In the aspect of the invention, the DC component change value of the pulse wave sensor signal is used to detect detachment of the biological information detection device. Therefore, even if various change factors are present in a DC component signal value, influences of the change factors can be minimized by a process of obtaining a change value, and thus it is possible to perform the detachment detection process with high accuracy.

In the aspect of the invention, the processing unit may perform the detachment detection process on the basis of the DC component change value of the pulse wave sensor signal in the predetermined period, and a second change value indicating a change in the DC component of the pulse wave sensor signal in a second period which includes the predetermined period and is longer than the predetermined period.

Consequently, even if a DC component change value in a relatively short period shows a trend which is similar to that in detachment (for example, in a case where an impact is applied to the biological information detection device), it is possible to minimize a possibility of false recognition that detachment is performed by using a DC component change value in a relatively long period.

In addition, in the aspect of the invention, the processing unit may determine that the biological information detection device is detached in a case where the DC component change value of the pulse wave sensor signal in the predetermined period exceeds a predetermined threshold value, and the second change value in the second period exceeds a second threshold value.

Consequently, it is possible to perform the detachment detection process based on a comparison process between each DC component change value and the threshold value.

Further, in the aspect of the invention, the biological information detection device may further include a body movement sensor that outputs a body movement signal, and the processing unit may determine that the biological information detection device is detached in a case where the DC component change value of the pulse wave sensor signal in the predetermined period exceeds a predetermined threshold value, and the body movement signal in a period corresponding to the predetermined period is equal to or smaller than a predetermined body movement threshold value.

Consequently, even if a DC component change value in a relatively short period shows a trend which is similar to that in detachment (for example, in a case where an impact is applied to the biological information detection device), it is possible to minimize a possibility of false recognition that detachment is performed by using a body movement signal.

In addition, in the aspect of the present invention, the processing unit may perform an initialization process of a parameter in a pulse wave determination process based on the pulse wave sensor signal in a case where detachment of the biological information detection device is detected through the detachment detection process.

Consequently, in a case where detachment is detected (the biological information detection device is in an unmounted state), it is possible to perform an initialization process of a parameter for use in the pulse wave determination process.

Further, in the aspect of the invention, the processing unit may perform a process of setting a window corresponding to a predetermined frequency range including a frequency which is determined as a pulse frequency in the past pulse wave determination process, and of preferentially determining a frequency included in the window as a pulse frequency, as the pulse wave determination process based on the pulse wave sensor signal. The processing unit may perform an initialization process of the window in a case where detachment of the biological information detection device is detected through the detachment detection process.

Consequently, in a case where detachment is detected, it is possible to perform an initialization process of a window which is a parameter for use in the pulse wave determination process.

In addition, in the aspect of the invention, in a case where detachment of the biological information detection device is detected through the detachment detection process, the processing unit may perform an initialization process of a filter coefficient of an adaptive enhancer which is applied to the pulse wave sensor signal.

Consequently, in a case where detachment is detected, it is possible to perform an initialization process of a filter coefficient of the adaptive enhancer.

Further, in the aspect of the invention, the processing unit may obtain a difference value between an i-th DC component value of the pulse wave sensor signal at an i-th (where i is a positive integer) sampling timing and a j-th DC component value of the pulse wave sensor signal at a j-th (where j is an integer satisfying j>i) sampling timing, as the DC component change value, and may perform the detachment detection process on the basis of the obtained DC component change value.

Consequently, it is possible to use a difference value between DC component values at two different sampling timings as a DC component change value in a predetermined period.

In addition, in the aspect of the invention, the processing unit may determine that the biological information detection device is detached in a case where the DC component change value of the pulse wave sensor signal in the predetermined period exceeds a predetermined threshold value.

Consequently, it is possible to perform the detachment detection process on the basis of a comparison process between a DC component change value and a threshold value.

Further, in the aspect of the invention, the processing unit may perform a remounting detection process of the biological information detection device on the basis of a third change value indicating a change in the DC component of the pulse wave sensor signal in a third period which is a period after detachment of the biological information detection device is detected through the detachment detection process.

Consequently, it is possible to determine not only detachment but also remounting on the basis of a DC component change value.

According to another aspect of the invention, there is provided a biological information detection device including a pulse wave detection unit that outputs a pulse wave sensor signal; and a processing unit that processes the pulse wave sensor signal, in which, in a case where detachment of the biological information detection device is detected, the processing unit gives an instruction for stopping recording or communication of pulse wave information based on the pulse wave sensor signal, or an instruction for recording or communication of pulse wave information correlated with information indicating that the pulse wave information is acquired in a detachment period.

Consequently, in the aspect of the invention, in a case where detachment of the biological information detection device is detected, an instruction for stopping recording or communication of pulse wave information is given, or an instruction for recording or communication of pulse wave information correlated with information indicating that the pulse wave information is acquired in a detachment period is given. Consequently, in a case where the biological information detection device is detached during measurement of pulse wave information, recording or the like of pulse wave information which does not reflect an actual pulse situation may not be performed, or pulse wave information which may possibly be inappropriate can be recorded or the like through correlation, and, as a result, it is possible to appropriately perform a process using the pulse wave information having undergone the recording or the communication.

In addition, in the aspect of the invention, in a case where remounting of the biological information detection device is detected, and a process of measuring pulse wave information based on the pulse wave sensor signal is successful, after detachment of the biological information detection device is detected, the processing unit may give an instruction for recording or communication of the pulse wave information.

Consequently, in a case where not only is remounting detected but it is also detected that a process of measuring pulse wave information is successful in an unmounted state of the biological information detection device, it is possible to perform recording or communication thereof.

Further, in the aspect of the invention, the processing unit may set a plurality of states including a mounted state corresponding to a case where the biological information detection device is mounted, an unmounted state corresponding to a case where the biological information detection device is detached, and an intermediate state corresponding to the middle between the mounted state and the unmounted state, and may give the instruction for stopping recording or communication or gives the instruction for recording or communication on the basis of a transition process between the plurality of set states.

Consequently, the process of the present embodiment can be realized as a state machine, and an intermediate state can be set in the state machine.

In addition, in the aspect of the invention, the processing unit may perform the transition process from the unmounted state to the intermediate state in a case where a mounting detection event is detected in the unmounted state, and may perform the transition process from the intermediate state to the mounted state in a case where a pulse wave information measurement successful event is detected in the intermediate state.

Consequently, in a case where not only is remounting detected but it is also detected that a process of measuring pulse wave information is successful in an unmounted state of the biological information detection device, it is possible to perform recording or communication thereof with the state machine using the intermediate state.

Further, in the aspect of the invention, the processing unit may perform a detection process of a detachment event and an impact occurrence event in the mounted state, determine that the biological information detection device is detached and perform the transition process from the mounted state to the unmounted state in a case where the detachment event is detected, and determine detection of an abnormality signal indicating that it is doubtful that the biological information detection device is detached and performs the transition process from the mounted state to the intermediate state in a case where the impact occurrence event is detected.

Consequently, it is possible to perform a flexible process such as direct transition or transition via the intermediate state in transition from the mounted state to the unmounted state.

In addition, according to still another aspect of the invention, there is provided a biological information detection device including a pulse wave detection unit that is provided with a pulse wave sensor which outputs a pulse wave sensor signal; and a processing unit that processes the pulse wave sensor signal, in which the processing unit gives an instruction for stopping display of pulse wave information based on the pulse wave sensor signal or performs a display switching process in a case where detachment of the biological information detection device is detected, and gives an instruction for displaying the pulse wave information in a case where remounting of the biological information detection device is detected and a process of measuring the pulse wave information based on the pulse wave sensor signal is successful after detachment of the biological information detection device is detected.

In the aspect of the invention, in a case where detachment of the biological information detection device is detected, display of pulse wave information is stopped or a display switching process is performed. A process of resuming display along therewith, or a switching process of returning display to an original state is performed when not only is remounting detected but it is also detected that a process of measuring pulse wave information is successful. Consequently, it is possible to present pulse wave information to a user in an appropriate aspect (including non-display of the pulse wave information depending on situations).

BRIEF DESCRIPTION OF THE DRAWINGS

FIG. 14 illustrates examples of states and events which are set in the present embodiment.

FIGS. 20(A) and 20(B) respectively illustrate a specific example of the event occurrence associated process and a specific example of the state associated process.

FIGS. 22(A) to 22(C) are diagrams for explaining evaluation results according to a method of the present embodiment.

DESCRIPTION OF EMBODIMENTS

Hereinafter, the present embodiment will be described. In addition, the present embodiment described below is not intended to improperly limit the content of the invention disclosed in the claims. Further, it cannot be said that all constituent elements described in the present embodiment are essential constituent elements of the invention.

1. Method of Present Embodiment

Figure 1:
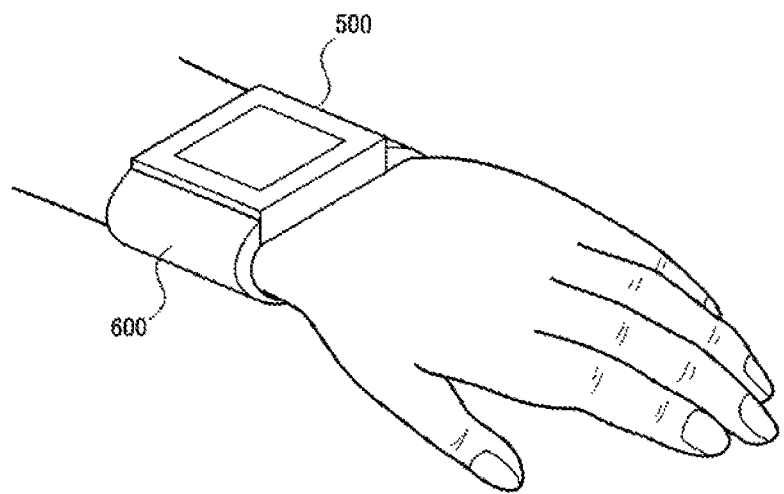
FIG. 1 illustrates an example of a mounted state of a biological information detection device according to the present embodiment.

First, a method of the present embodiment will be described. As illustrated in FIG. 1, a biological information detection device which is mounted on the arm or the like has been widespread. Biological information detected by the biological information detection device may be, for example, pulse wave information such as a pulse rate, and may be information indicating an activity amount such as the number of steps. The pulse wave information may be obtained by using a pulse wave sensor, and the information such as the number of steps may be obtained by using an acceleration sensor or the like.

Figure 2:
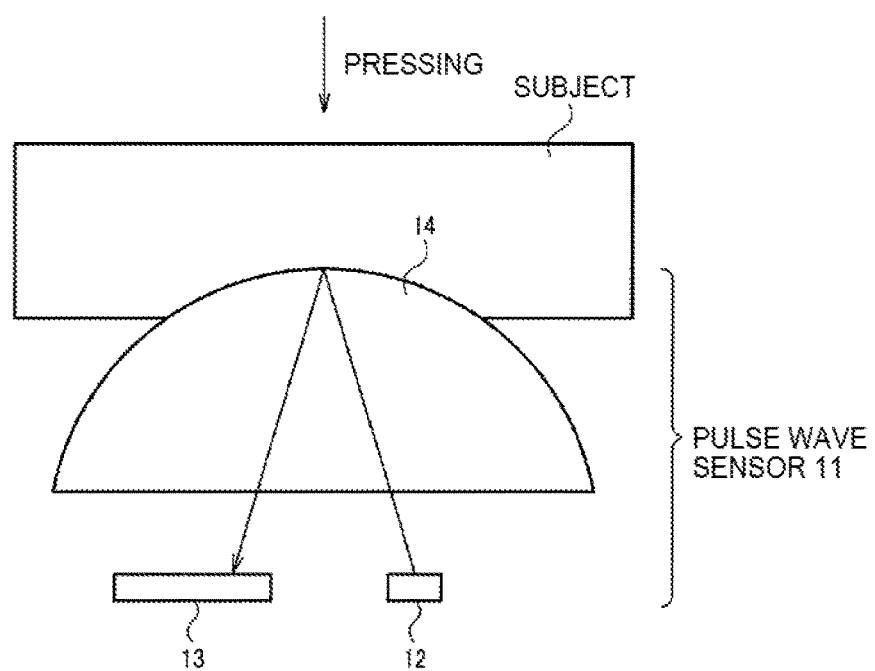
FIG. 2 illustrates a configuration example of a pulse wave sensor.

A biological information detection device as illustrated in FIG. 1 is based on the biological information detection device being appropriately mounted on a user's arm or the like. For example, in a case where a pulse wave sensor includes an LED and a photodiode (PD), the pulse wave sensor acquires a pulse wave sensor signal by detecting reflected light which is obtained when irradiation light from the LED is reflected from a living body, with the PD. In this case, when taking into consideration the irradiation light being appropriately applied to the living body, the reflected light from the living body being detected with the PD at a sufficient intensity, detection of light other than the reflected light being restricted in the PD, and the like, for example, as illustrated in FIG. 2, the pulse wave sensor is required to have a positional relationship of being in close contact with the living body.

In a case of the wristwatch type biological information detection device as illustrated in FIG. 1, such a positional relationship is realized by appropriately fixing the biological information detection device to the user's arm after a pulse wave sensor is provided on a rear side (a side which is in contact with the user's arm) of a dial portion. In other words, the biological information detection device being appropriately mounted is a condition which is required in calculation or the like of pulse wave information using the pulse wave sensor.

In addition, it is known that appropriate pressing is required to be applied in order to detect an appropriate pulse wave sensor signal in the pulse wave sensor. The pressing here indicates pressure of the pulse wave sensor portion for the living body as illustrated in FIG. 2. In other words, if the biological information detection device is in an appropriate mounted state, an appropriate pressure can be applied by a holding mechanism such as a band, and a pulse wave signal can also be obtained. Thus, it can be said that a mounted state of the biological information detection device is important.

Conversely, if biological information is detected in an unmounted state of the biological information detection device, an inappropriate result is obtained. In the pulse wave sensor, external light which is expected to be considerably stronger than reflected light from the living body is detected by the PD. In this case, even if pulse wave information such as a pulse rate is obtained by using a pulse wave sensor signal, the pulse wave information does not reflect a real pulse rate of the user. For this reason, in a case of performing a process of generating health advice for the user by using the obtained pulse rate or the like, there is a concern that an inappropriate process may be performed. In addition, the same problem also occurs in a process using information other than a pulse wave sensor signal. For example, in a case where the number of steps is detected on the basis of sensor information from an acceleration sensor, a process is performed on the basis of an acceleration detection value based on walking. However, since influences on an acceleration detection value are different in states in which the biological information detection device is mounted on the arm and is not mounted (for example, a state in which the biological information detection device is put in a bag or a state in which a band portion is grasped with the hand), the same process cannot be performed.

In other words, a mounted state or an unmounted state of the biological information detection device is very important information. However, if a user inputs information indicating a mounted state and an unmounted state of the biological information detection device, an operation is complicated and is not desirable. Therefore, it is necessary to automatically determine a mounted state and an unmounted state.

However, since a biological information detection device of the related art mounted on the arm or the like is required to be small-sized and lightweight, there is a restriction in battery capacity or the like in most cases, and thus usage thereof for a long period of time is not expected. For this reason, for example, when a pulse rate during exercise is measured, there is the general use case where the device is mounted and is powered on right before the exercise, and the device is powered off after the exercise. In this case, since it is naturally expected that the biological information detection device is in an appropriate mounted state in a situation in which the biological information detection device measures pulse wave information, there is a low necessity for taking into consideration a danger in which an inappropriate signal is detected in an unmounted state, and pulse wave information is calculated on the basis of the signal.

As a result, a process may be performed by regarding acquired pulse wave information pieces as appropriate pulse wave information pieces which are all acquired in a mounted state without being aware of a mounted state and an unmounted state. In addition, in a method of detecting an attached or a detached state (left state), proposed in the related art, a battery related process such as transition to a power saving mode or turning off display is performed in a non-attachable or detachable state or a left state, and treatment of calculated pulse wave information is not disclosed in the related art.

However, the present applicant implements a biological information detection device which can perform continuous operations for a long period of time while realizing a small size and a light weight by taking into consideration the structure of the biological information detection device including a pulse wave sensor, content of a calculation process of pulse wave information based on a pulse wave sensor signal, or the like. In this case, the biological information detection device does not detect biological information only in a specific situation (for example, during exercise) but for a long period of time (a day in a narrow sense) including business time or sleeping time, and can use the biological information as a "life log".

In detection of the life log, since a user is not forced to wear the biological information detection device for 24 hours in 365 days, a lot of situations may occur in which the biological information detection device is in an unmounted state while measuring a pulse wave sensor signal. In this case, if appropriate pulse wave information which is acquired in a mounted state and inappropriate pulse wave information which is acquired in an unmounted state are treated in an equivalent manner, this causes problems in processes using the pulse wave information.

Therefore, the present applicant proposes a method in which a mounted state or an unmounted state is detected according to a certain method, and if the unmounted state is determined, an instruction for stopping recording and communication of calculated pulse wave information or an instruction for recording and communication correlated with information indicating the unmounted state is given. In the above-described way, it is possible to appropriately perform a process using recorded pulse wave information, or a process using pulse wave information, performed in an external electronic apparatus which is a communication destination. If the instruction for stopping recording and communication is given, pulse wave information in the unmounted state is not acquired from the beginning in the process using the pulse wave information. In addition, if the instruction for recording and communication correlated with information indicating the unmounted state is given, it is possible to lower the priority of pulse wave information in the unmounted state or to perform determination such as the pulse wave information is not used in a process at all.

In addition, the present applicant also proposes a method of detecting attachment and detachment by using a DC component change value of a pulse wave sensor signal. PTL 1 discloses that a voltage value of a pulse wave sensor differs in a mounted state and an unmounted state. Therefore, a mounted state and an unmounted state may be determined on the basis of such a voltage value.

However, a pulse wave sensor signal (an output voltage value of the pulse wave sensor) changes depending on various factors. For example, an amount of external light detected by the PD differs in a case where a user stays outdoors in fine weather in which an influence of external light is great and a case where the user stays in a dark room, and thus the magnitude of the pulse wave sensor signal also differs. For example, since there is a high possibility that external light is detected by the PD in an unmounted state, a pulse wave sensor signal considerably changes depending on situations of the external light. In addition, even in a mounted state, it is hard to completely block introduction of external light, and thus a signal value may change due to the external light.

Further, it is known that attenuation rates of LED light differ due to hemoglobin or melanin in the skin. Still further, an amount of hemoglobin or melanin differs in different users, and may change due to a change in a condition or the like even for the same user. In other words, a pulse wave sensor signal in a mounted state changes due to an individual difference for each user, or a change in a condition or the like of the same user.

In addition, it is known that a pulse wave sensor signal also changes due to pressing. Further, since appropriate pressing is influenced by an internal pressure which is pressure inside a blood vessel, there is an individual difference for each user or a difference even for the same user. Still further, it is not ensured that each user applies the same pressing every time, that is, the user wears a holding mechanism such as a band under the same conditions every time. In other words, a pulse wave sensor signal in a mounted state also changes due to the pressing.

As mentioned above, pulse wave sensor signals change in a mounted state and an unmounted state, respectively, and thus it is hard to set a threshold value which causes the mounted state and the unmounted state to be clearly determined. In other words, even if a threshold value determination is simply performed by using an output voltage value of the pulse wave sensor, it is hard to determine a mounted state and an unmounted state with high accuracy.

Therefore, the present applicant proposes a method of determining a mounted state and an unmounted state on the basis of a DC component change value of a pulse wave sensor signal. As described above, since a DC component value itself changes due to various factors, it is hard to set an appropriate threshold value, but it is possible to determine attachment and detachment with high accuracy by using a DC component change value. For example, a difference value between the maximum value and the minimum value in a predetermined period may be obtained as the DC component change value. Since a change in the pulse wave sensor signal due to the above-described factors influences both of the maximum value and the minimum value, it is possible to cancel (minimize, in a broad sense) the influence by taking a difference value therebetween.

Figure 3:
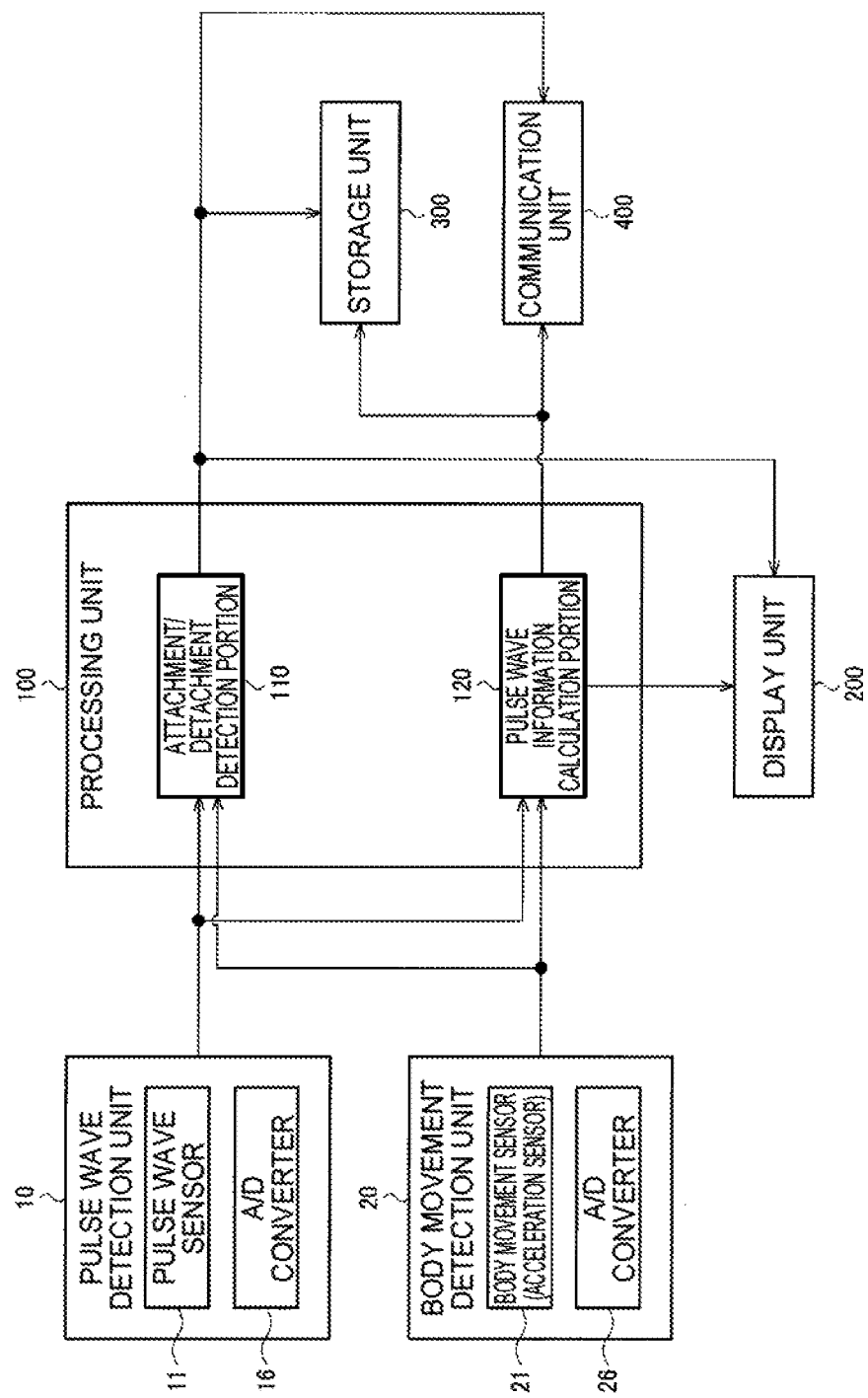
FIG. 3 illustrates a configuration example of the biological information detection device according to the present embodiment.

The biological information detection device of the present embodiment includes, as illustrated in FIG. 3, a pulse wave detection unit 10 which outputs a pulse wave sensor signal and a processing unit 100 which processes the pulse wave sensor signal. The processing unit 100 performs a process of detecting detachment of the biological information detection device on the basis of a DC component change value of the pulse wave sensor signal in a predetermined period.

Consequently, as described above, it is possible to determine a mounted state and an unmounted state of the biological information detection device with high accuracy by minimizing an influence of a change in the pulse wave sensor signal due to various factors.

In addition, even if the biological information detection device is in a mounted state, in a case where a strong impact is applied to the biological information detection device, there is a concern that a false determination of being in an unmounted state may be performed despite a mounted state. This is because, if an excessive impact is unintentionally applied to the vicinity of a mounting part without detaching the biological information detection device from the arm, a pulse wave sensor may be separated from the skin for a moment. Also in this case, since the pulse wave sensor signal (voltage value) shows a characteristic change which is similar to a case where transition is made from a mounted state to an unmounted state, there is a possibility of wrong detection as if a pulsimeter is detached from the arm despite actually being mounted on the arm.

Therefore, in the present embodiment, a method is also proposed in which floating of the pulse wave sensor due to an impact and an unmounted state are appropriately identified. This method may use a DC component change value (second change value) of the pulse wave sensor signal in a second period which is longer than a target predetermined period in a simple attachment/detachment detection process, and may use a body movement signal from a body movement sensor such as an acceleration sensor. Details of each thereof will be described later.

Hereinafter, a system configuration example of the biological information detection device according to the present embodiment will be described prior to description of a specific process of the above-described attachment/detachment detection method for the biological information detection device. In addition, a description will be made of setting of events used for a state and state transition, or a state transition diagram in a case where the process of the present embodiment is realized as a state machine.

2. System Configuration Example

FIG. 3 illustrates a system configuration example of the biological information detection device according to the present embodiment. As illustrated in FIG. 3, the biological information detection device includes the pulse wave detection unit 10, a body movement detection unit 20, the processing unit 100, a display unit 200, a storage unit 300, and a communication unit 400. However, the biological information detection device and each unit of the biological information detection device are not limited to the configuration illustrated in FIG. 3, and may be variously modified by omitting or changing some of the constituent elements or adding other constituent elements thereto.

The pulse wave detection unit 10 outputs a signal on the basis of sensor information (pulse wave sensor signal) from a pulse wave sensor. The pulse wave detection unit 10 may include, for example, a pulse wave sensor 11 and an A/D converter 16.

The pulse wave sensor 11 is a sensor which detects a pulse wave signal, and may be, for example, a photoelectric sensor. In addition, in a case where the photoelectric sensor is used as the pulse wave sensor 11, a sensor may be used which is configured to cut off a signal component of external light such as sunlight. This may be realized by a configuration in which, for example, a plurality of photodiodes are provided, and difference information is obtained through a feedback process using signals therefrom.

FIG. 2 is a schematic diagram in which a portion including the pulse wave sensor 11 of the biological information detection device is enlarged. As illustrated in FIG. 2, the pulse wave sensor 11 includes an LED 12 which applies light, a photodiode (PD) 13 which receives reflected light obtained when the applied light is reflected from a living body, and a convex portion 14 which comes into contact with the living body. The pulse wave sensor 11 of the present embodiment includes the convex portion 14 illustrated in FIG. 2 and thus efficiently applies pressure (pressing) to the living body. Here, it is known that, during detection of pulse wave information, detection accuracy can be improved by adjusting pressing indicating pressure for a living body around a pulse wave sensor. The convex portion 14 illustrated in FIG. 2 has a structure in which pressing adjustment is taken into consideration, but a method related to the pressing adjustment is deviated from a main purpose of the method of the present embodiment, and thus detailed description thereof will be omitted.

The A/D converter 16 performs an A/D conversion process on a pulse wave sensor signal so as to output a digital signal.

The body movement detection unit 20 outputs a signal (body movement signal) corresponding to a body movement on the basis of sensor information from various sensors. The body movement detection unit 20 may include, for example, a body movement sensor (an acceleration sensor in a narrow sense) 21 and an A/D converter 26. However, the body movement detection unit 20 may include other sensors (for example, a pressure sensor or a gyro sensor), or an amplifier which amplifies a signal or the like. In addition, a plurality of types of sensors are not required to be provided, and a single type of sensor may be provided. The A/D converter 26 performs an A/D conversion process on the body movement signal so as to output a digital signal.

The processing unit 100 performs various processes on the basis of the pulse wave sensor signal or the body movement signal. The processing unit 100 may include an attachment/detachment detection portion 110 and a pulse wave information calculation portion 120.

The attachment/detachment detection portion 110 performs a process of detecting attachment or detachment of the biological information detection device on the basis of the pulse wave sensor signal from the pulse wave detection unit 10. As illustrated in FIG. 3, the attachment/detachment detection portion 110 may also use the body movement signal from the body movement detection unit 20. The attachment/detachment detection portion 110 performs, specifically, a determination of a mounted state or an unmounted state, but, as will be described later, may perform a process in which an intermediate state between the mounted state and the unmounted state is also taken into consideration. Details of a process in the attachment/detachment detection portion 110 will be described later.

In addition, the attachment/detachment detection portion 110 is connected to the display unit 200, the storage unit 300, and the communication unit 400, and gives an instruction regarding display, storage, and communication on the basis of a result of an attachment or detachment detection process.

The pulse wave information calculation portion 120 performs a calculation process of pulse wave information such as a pulse rate on the basis of the pulse wave sensor signal. It is known that an AC component of the pulse wave sensor signal shows a signal having periodicity corresponding to a pulse cycle of a user. Therefore, the pulse wave information calculation portion 120 may perform a process of obtaining a peak frequency as a pulse frequency by performing a signal process such as FFT on the AC component of the pulse wave sensor signal. Alternatively, a pulse rate which is widely used may be obtained by multiplying the obtained pulse frequency by 60.

However, a process in the pulse wave information calculation portion 120 is not limited thereto, and may be variously modified. For example, without conversion into a frequency axis, a frequency of an AC component of the pulse wave sensor signal may be obtained on the basis of rising and falling of the signal on a time axis. In addition, since it is known that body movement noise originating from a body movement of the user is included in the pulse wave sensor signal, a process of reducing the body movement noise may be performed by using the body movement signal. Further, various methods are known for calculation of pulse wave information based on the pulse wave sensor signal and the body movement signal, and are widely applicable in the present embodiment, and thus detailed description thereof will not be repeated any more.

The pulse wave information calculation portion 120 outputs pulse wave information which is a calculation result to the display unit 200, the storage unit 300, and the communication unit 400.

The display unit 200 displays various display screens which are used to present the calculated pulse wave information, and may be implemented by using, for example, a liquid crystal display or an organic EL display.

The storage unit 300 is a work area of the processing unit 100 and the like, and a function thereof may be realized by a memory such as a RAM, or a hard disk drive (HDD). In addition, the storage unit 300 stores the pulse wave information calculated by the pulse wave information calculation portion 120.

The communication unit 400 is connected to other devices via a network and performs communication of various pieces of information. The communication unit 400 transmits the pulse wave information calculated by the pulse wave information calculation portion 120 to other electronic devices. In addition, the network here may be implemented by a wide area network (WAN) or a local area network (LAN), and may be of a wired or wireless type.

FIG. 1 illustrates an example in which the biological information detection device of the present embodiment is mounted. FIG. 1 illustrates an example in which the biological information detection device is a wristwatch type device. A base section 500 including the pulse wave sensor 11 and the display unit 200 is mounted on the left wrist of a subject (user) by a holding mechanism 600 (for example, a band).

3. Specific Method of Detecting Attachment and Detachment

Next, a specific method of detecting attachment and detachment will be described. First, a description will be made of a fundamental method using a DC component change value of a pulse wave sensor signal, and then a description will be made of a method of discriminating a case where an impact is applied to the biological information detection device therefrom.

3.1 Fundamental Method Using DC Component Change Value

Figure 4:
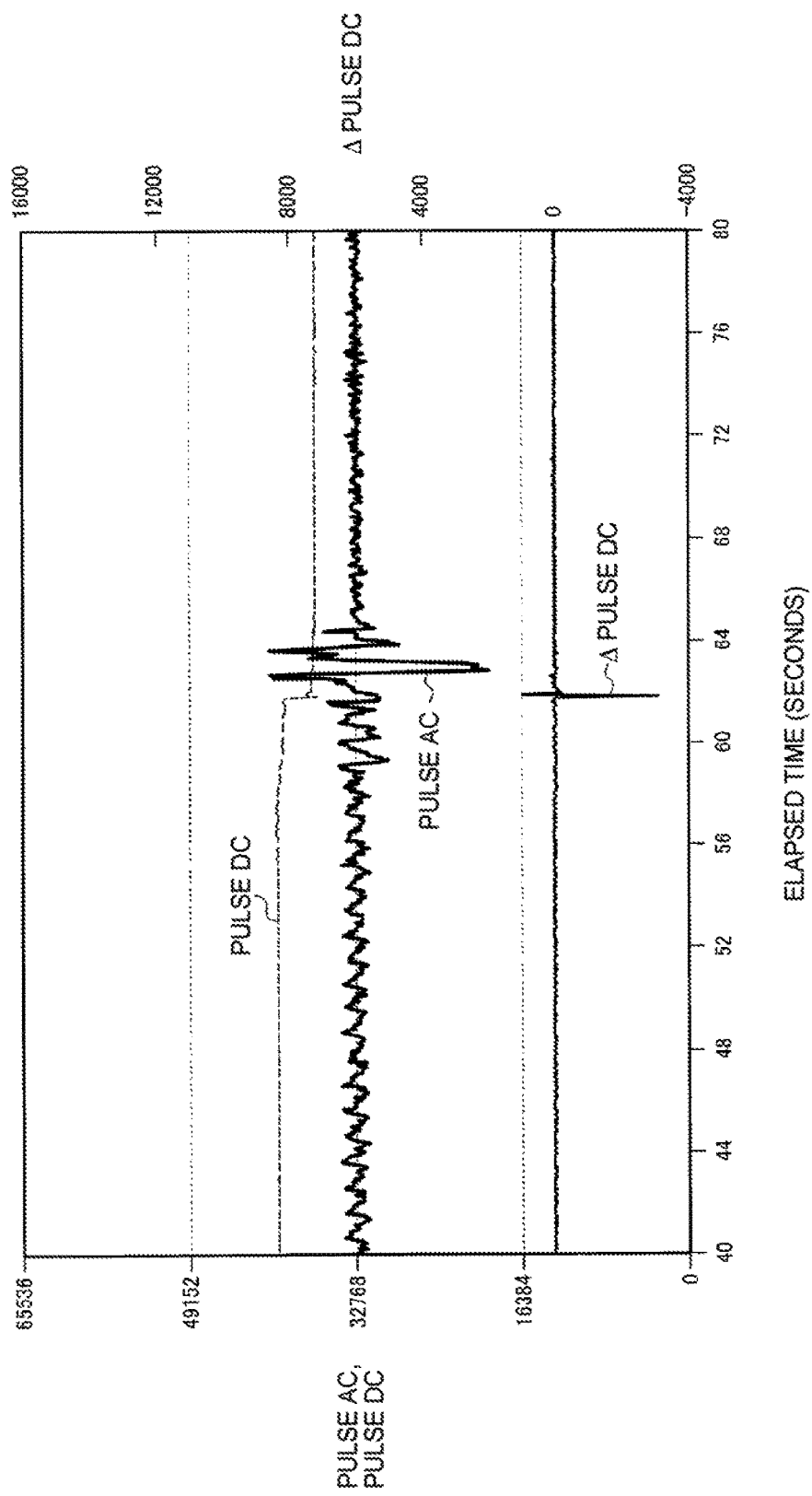
FIG. 4 illustrates a waveform example of a pulse wave sensor signal when the biological information detection device is detached.

FIG. 4 illustrates a change in a pulse wave sensor signal in a case where a state changes from a mounted state to an unmounted state. Herein, the stronger the light detected by the PD 13 of the pulse wave sensor 11, the smaller the output voltage value of the pulse wave sensor signal. However, a relationship between an amount of detected light and an output voltage value changes depending on a configuration of the pulse wave sensor 11, and thus there may be a case where the larger the amount of detected light, the greater the output voltage value.

In FIG. 4, the biological information detection device is detached when the elapsed time is about 62 seconds. As can be seen from FIG. 4, an AC component (pulse AC) of the pulse wave sensor signal shows a signal having periodicity corresponding to a pulse up to about 56 seconds in a mounted state, then shows a signal which does not correspond to the pulse after the detachment is completed since a signal waveform is disturbed due to the detachment operation, and thus shows a waveform having no periodicity.

On the other hand, a DC component (pulse DC) of the pulse wave sensor signal has a substantially constant value in a stably mounted state, and has a substantially constant value which is different from that in the mounted state, in a stably unmounted state after the detachment is completed. In addition, the value in the unmounted state is smaller than the value in the mounted state. However, as described above, both of a value in the mounted state and a value in the unmounted state change due to various factors, and thus it is hard to detect attachment and detachment with high accuracy in a process of comparing each value with a threshold value.

Therefore, in the present embodiment, as indicated by Δpulse DC in FIG. 4, a DC component change value of the pulse wave sensor signal is used. As can be seen from FIG. 4, the DC component change value is a value close to 0 in each of the mounted state and the unmounted state, but becomes a great absolute value at a timing (detachment timing) at which the mounted state changes to the unmounted state. In addition, a value in the mounted state and a value in the unmounted state change due to various factors, but the DC component change value which is a difference value therebetween is free from influences of the various factors. Therefore, it is possible to detect attachment and detachment with high accuracy by using the DC component change value regardless of a situation of external light, a difference in a user's hemoglobin, or a change in a pressure state.

Here, a process of comparing a DC component change value ΔDC1 with a predetermined threshold value Th1 is performed, and detachment is determined if the DC component change value is greater than the predetermined threshold value (ΔDC1>Th1). In addition, FIG. 4 illustrates a case where ΔDC1>Th1 is satisfied in the mounted state, and thus it is determined that the mounted state changes to the unmounted state, that is, detachment is performed. However, also in a case where the unmounted state changes to the mounted state (that is, remounting is performed), the DC component change value becomes a great value although a sign of the DC component change value differs. Thus, in a case of the unmounted state, whether or not ΔDC1>Th1 is satisfied may be used to determine detection of remounting.

Here, a change in a DC component signal value during detachment is expected to occur in a fairly short period of time. The pulse wave sensor 11 in the mounted state is in close contact with the living body as illustrated in FIG. 2, and if the pulse wave sensor 11 floats from the skin due to detachment, a change in the DC component occurs as shown in the vicinity of 62 seconds in FIG. 4. In addition, as in a case of detecting an impact as will be described later, the DC component considerably changes due to the biological information detection device just slightly floating. In other words, since the DC component considerably changes in a period in which the biological information detection device floats from the state of being in contact with the skin, it is unlikely that a long time (for example, an order of several seconds) is required for the device to float.

Figure 5A:
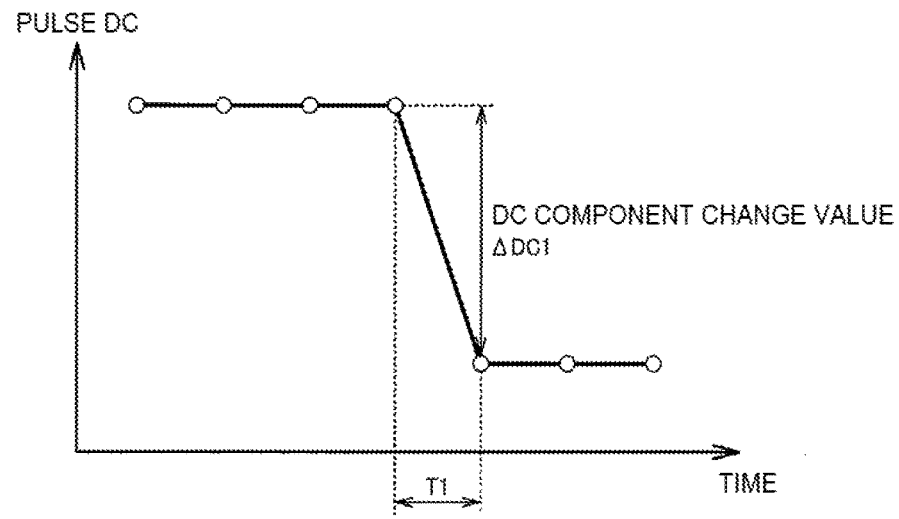
FIGS. 5(A) and 5(B) are diagrams for explaining a change value of a DC component of the pulse wave sensor signal in a predetermined period.

Therefore, in the present embodiment, the DC component change value ΔDC1 is obtained on the basis of a DC component in a predetermined period T1 which is fairly short. The period T1 here may be, for example, a period corresponding to one cycle of sampling cycles of the pulse wave sensor 11. If a sampling frequency of the pulse wave sensor 11 is 16 Hz, the sampling cycle and the predetermined period are 1/16 seconds. In this case, a difference value between DC components of the pulse wave sensor signal, which are temporally adjacent to each other, becomes a DC component change value as illustrated in FIG. 5(A).

Figure 5B:
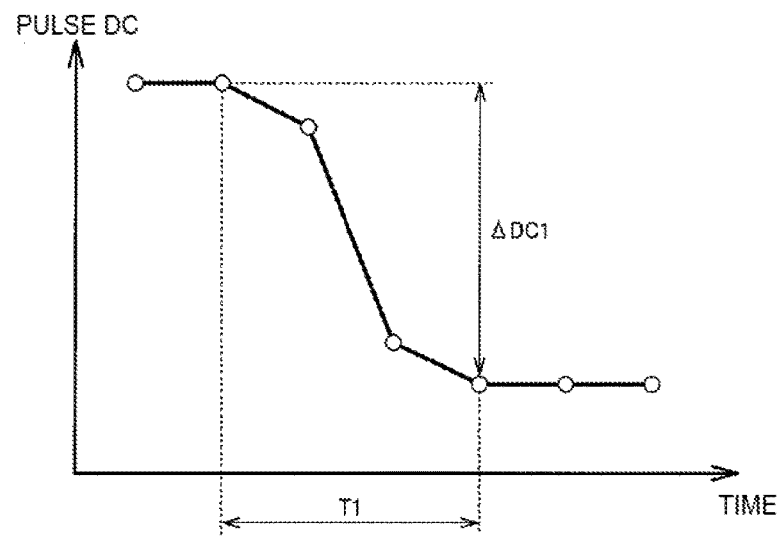

However, the predetermined period T1 is not limited thereto, and a period corresponding to a plurality of sampling cycles may be set. For example, FIG. 5(B) illustrates a case where a period corresponding to three cycles is set as T1. In this case, there may be various methods of obtaining a DC component change value, but, for example, as illustrated in FIG. 5(B), a difference value between the maximum value and the minimum value of a DC component signal value included in T1 may be obtained.

3.2 Impact Detection Process

As described above, detachment of the biological information detection device can be detected by performing a process of comparing the DC component change value ΔDC1 of the pulse wave sensor signal in the predetermined period T1 with the predetermined threshold value Th1. However, in a case where a strong impact is applied to the biological information detection device, the biological information detection device and the pulse wave sensor 11 provided in the biological information detection device may float from a living body (skin). In this case, the PD 13 of the pulse wave sensor 11 does not appropriately detect reflected light obtained when irradiation light from the LED 12 is reflected from the living body, and there is a possibility that external light may enter a gap between the skin and the biological information detection device. For this reason, a pulse wave sensor signal shows the same characteristics as in an unmounted state in a period in which the pulse wave sensor 11 floats.

Figure 6A:
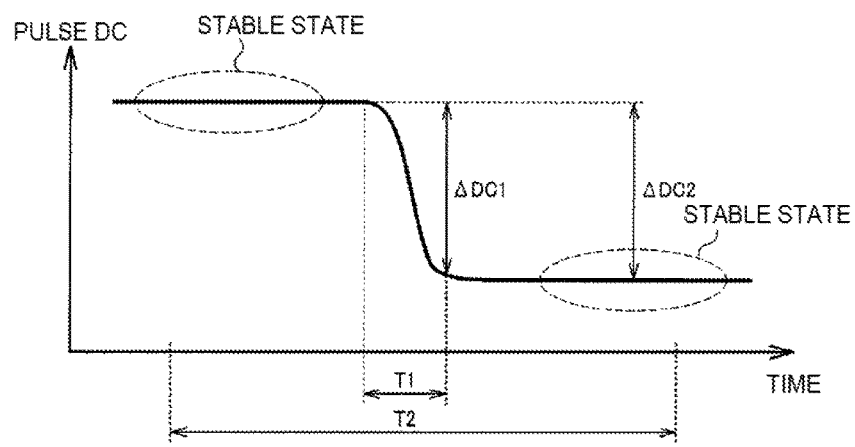
FIGS. 6(A) and 6(B) are diagrams for explaining a difference between waveforms of the DC component due to detachment and an impact.
Figure 6B:
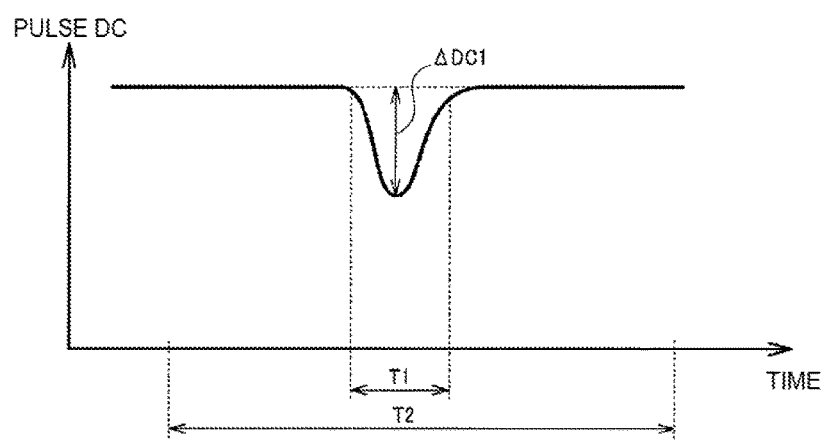

Specifically, it is observed that a temporary reduction in a DC component value occurs as illustrated in FIG. 6(B) in a case where an impact is applied in the same manner as in a case where a DC component of the pulse wave sensor signal changes as illustrated in FIG. 6(A) (a reduction in the example illustrated in FIG. 6(A)) when detachment is performed.

Therefore, the DC component change value ΔDC1 in the predetermined period T1 becomes a fairly great value as illustrated in FIG. 6(B) even in a case of detecting an impact without the actual occurrence of detachment, and exceeds Th1 depending on cases. In this case, a wrong determination of transfer to an unmounted state through detachment is performed despite continuity of the mounted state and thus this is not desirable.

Figure 7A:
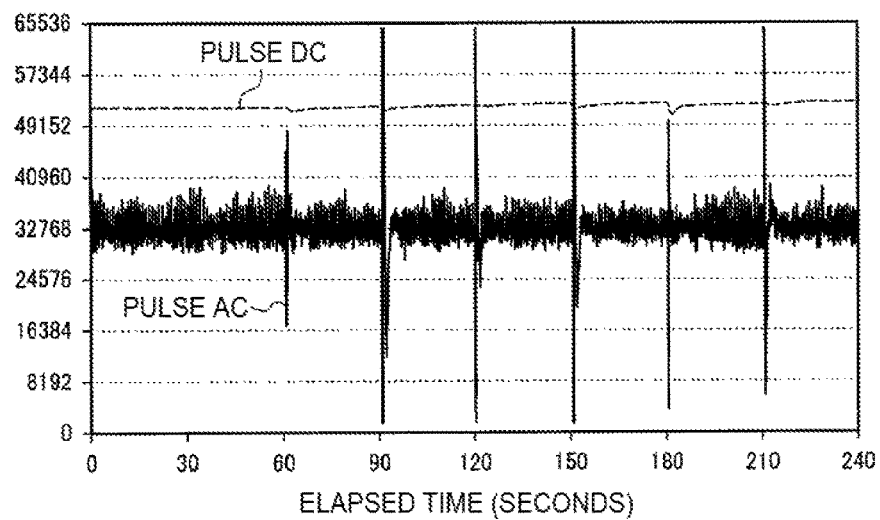
FIGS. 7(A) and 7(B) illustrate waveform examples of the pulse wave sensor signal in a case where an impact is applied.
Figure 7B:
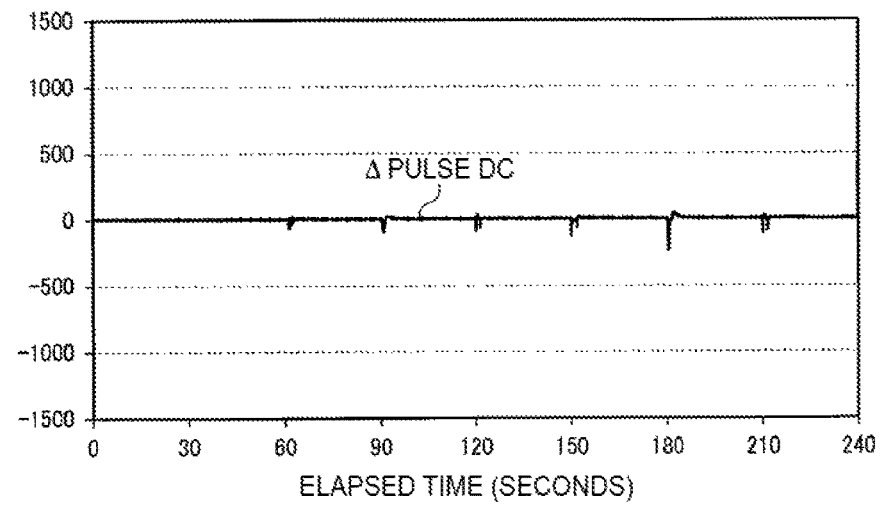

A specific example will be described with reference to the drawings. FIGS. 7(A) and 7(B) illustrate a change in a pulse wave sensor signal in a case where an impact is applied to the biological information detection device. In FIGS. 7(A) and 7(B), impacts are applied to the biological information detection device at an interval of 30 seconds from the time when 60 seconds elapse. As illustrated in FIG. 7(A), it is observed that both an AC component and a DC component of the pulse wave sensor signal change to great values at the timing at which the impact is applied. Therefore, the DC component change value ΔDC1 also becomes a fairly great value at the timing at which the impact is applied as illustrated in FIG. 7(B). In addition, in FIG. 7(B), a difference value between the DC components at adjacent timings is used as the DC component change value, and corresponds to a case where the predetermined period T1 is set as one sampling cycle.

Figure 10A:
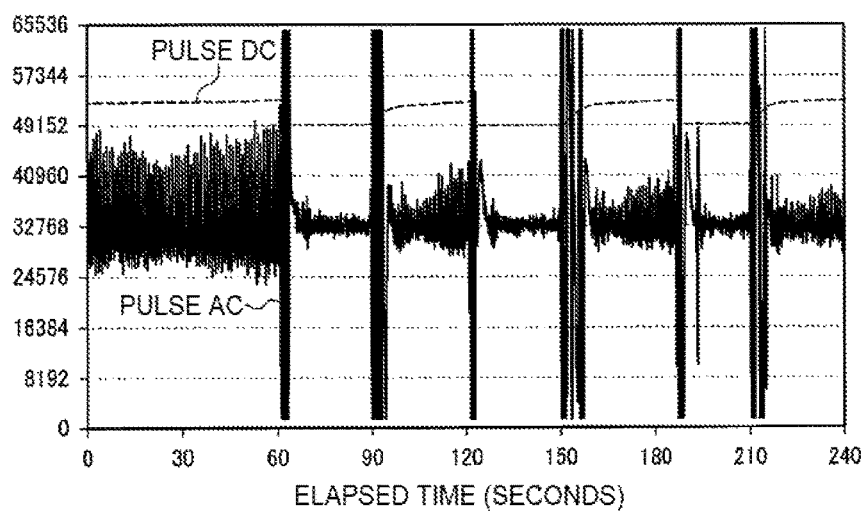
FIGS. 10(A) and 10(B) illustrate waveform examples of the pulse wave sensor signal in a case where the biological information detection device is attached and detached.
Figure 10B:
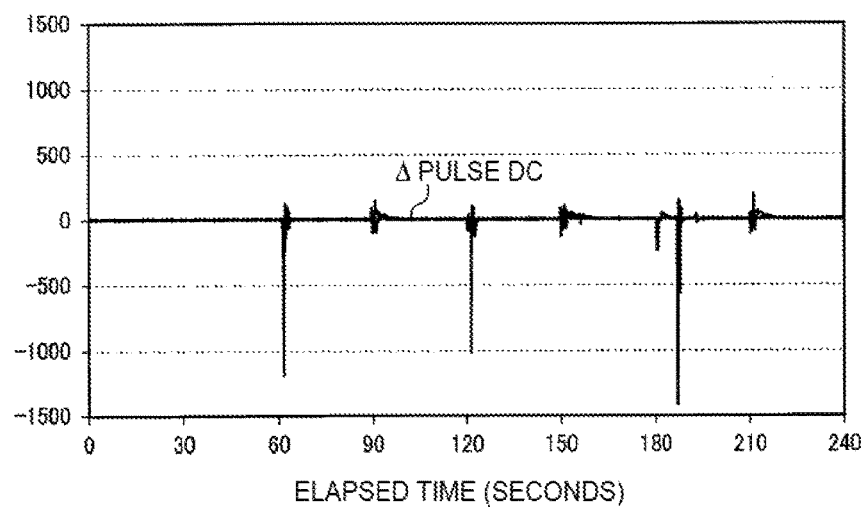

In addition, FIGS. 10(A) and 10(B) illustrate changes in the pulse wave sensor signal in a case where detachment and remounting are performed. In FIGS. 10(A) and 10(B), the biological information detection device is detached from the arm at the times when 60 seconds, 120 seconds, and 187 seconds elapse, and the biological information detection device is mounted on the arm at the times when 90 seconds, 150 seconds, and 206 seconds elapse. As illustrated in FIG. 10(A), it is observed that both an AC component and a DC component of the pulse wave sensor signal change to great values at the timings corresponding to both of the detachment and the remounting. For this reason, as illustrated in FIG. 10(B), the DC component change value ΔDC1 also becomes a great value at the corresponding timings. Further, as illustrated in FIG. 10(B), ΔDC1 becomes a considerably great value in the detachment, whereas ΔDC1 becomes a relatively small value.

When FIG. 7(B) is compared with FIG. 10(B), in a case where both discrimination between detachment and an impact and discrimination between remounting and an impact are performed, a difference between values of ΔDC1 is not great (specifically, values of ΔDC1 are similar to each other in a case of the remounting and the impact), and thus it is difficult to perform the discrimination only by using ΔDC1. For example, in a case where a threshold value Th1 for detecting both the detachment and the remounting is set, there is a high possibility that a value of ΔDC1 obtained when an impact is applied may also exceed Th1.

Therefore, in the present embodiment, a determination of impact detection may be performed along with a determination using ΔDC1 in the period T1. In addition, even in a case where ΔDC1 exceeds Th1, if an impact is detected, a DC component change value originates from the impact, and thus it is determined that detachment is not performed. If ΔDC1 exceeds Th1, and an impact is not detected, it may be determined that detachment is performed.

In the present embodiment, an impact determination may be performed by using a DC component change value ΔDC2 in a second period T2 which is different from the period T1, the impact determination may be performed by using a body movement signal from the body movement sensor, and may be performed by using both of the two. Hereinafter, each method will be described.

First, a description will be made of a method using ΔDC2 in the period T2. As described above, since the DC component change value ΔDC1 in the period T1 becomes a fairly great value both in a case of detachment and in a case of an impact, highly accurately discrimination therebetween is unlikely to be performed. However, when stable states in which a DC component signal value is stabilized before and after the period T1 are observed, detachment and an impact can be discriminated from each other.

As illustrated in FIG. 4 or 6, it can be seen that the DC component signal value is in a stable state in which a great change does not occur in a situation in which a mounted state lasts or in a situation in which an unmounted state lasts. Therefore, in a case where a mounted state changes to an unmounted state due to actual detachment, as illustrated in FIG. 6(A), a value corresponding to the mounted state can be stably obtained before the DC component in the period T1 changes (specifically, before the DC component is influenced by a detachment operation), and a value corresponding to the unmounted state can be stably obtained after the DC component in the period T1 changes (specifically, after the influence of the detachment operation sufficiently settles). Therefore, if the DC component change value ΔDC2 is obtained in the period T2 which includes the period T1 and is thus longer than the period T1, ΔDC2 becomes a fairly great value in a case where detachment is performed. Here, as described above, the period T2 is, for example, a period with a length including both a timing before the DC component signal value is influenced by a detachment operation and a timing after the influence is sufficiently reduced.

In contrast, in a case where detachment is not performed but an impact is applied, states both before and after the DC component in the period T1 changes correspond to the mounted state. Therefore, as illustrated in FIG. 6(B), if the DC component change value ΔDC2 in the period T2 is obtained, ΔDC2 becomes a value close to 0.

From the above description, it is possible to perform an impact determination on the basis of the comparison process between ΔDC2 in the period T2 and a predetermined threshold value Th2. Specifically, if ΔDC2 is greater than Th2, it may be determined that an impact is not detected, and if ΔDC2 is equal to or smaller than Th2, it may be determined that an impact is detected.

In other words, when combined with a determination using ΔDC1 in the period T1, if ΔDC1>Th1 and ΔDC2>Th2, it is determined that the biological information detection device is detached, and if ΔDC1>Th1 and ΔDC2≤Th2, it is determined that detachment is not performed but an impact is applied.

In addition, an impact may be detected on the basis of a body movement signal from the body movement sensor. As described above, a case where there is a possibility of false recognition as detachment is a case where the biological information detection device floats, and, specifically, a case where a strong impact is applied to the biological information detection device. Therefore, if a motion sensor which detects a motion is provided in the biological information detection device, the impact can be detected by using the motion sensor.

Generally, a body movement sensor is provided in the biological information detection device in order to detect body movement information (for example, information indicating the number of steps, or information regarding an exercise load) as biological information or to reduce body movement noise included in a pulse wave sensor signal. Therefore, an impact detection sensor may be separately provided, but, in most cases, the body movement sensor may be used for impact detection and other processes. Hereinafter, a description will be made of an example in which an acceleration sensor is used as the body movement sensor.

Figure 8A:
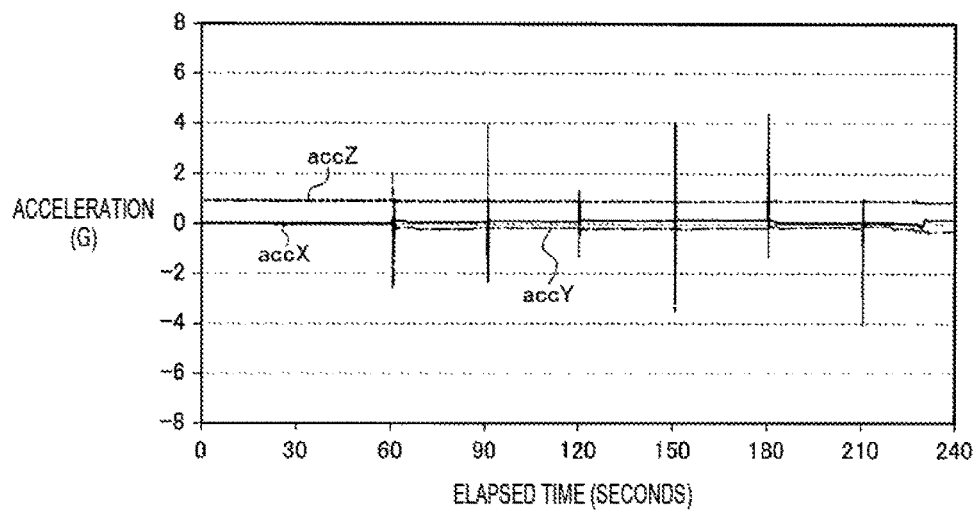
FIGS. 8(A) and 8(B) illustrate waveform examples of an acceleration detection value in a case where an impact is applied.
Figure 8B:
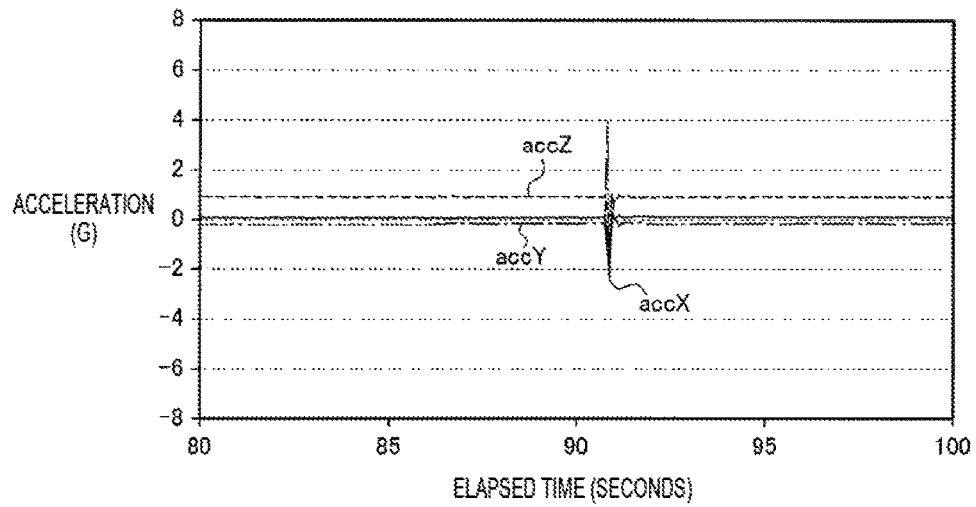

In the same manner as in FIGS. 7(A) and 7(B), FIG. 8(A) illustrates changes in sensor information (acceleration detection value) from the acceleration sensor in a case where impacts are applied to the biological information detection device at an interval of 30 seconds from the time when 60 seconds elapse. Herein, a three-axis acceleration sensor is assumed, and a change in acceleration on each of XYZ axes is illustrated. In addition, FIG. 8(B) illustrates that a location around a portion where the elapsed time is 90 seconds is enlarged in order to observe an acceleration change in detail when one impact is applied. As can be seen from now on, an acceleration detection value becomes about ±2 G to ±4 G at a timing corresponding to the impact. In addition, it can be seen from FIG. 8(B) that a signal caused by the impact appears in the acceleration detection value for about one second after the impact is applied.

Figure 11A:
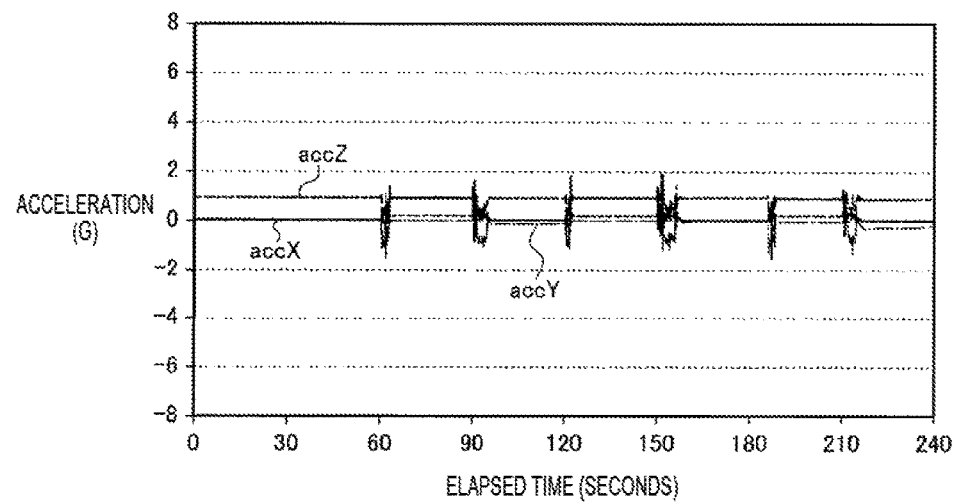
FIGS. 11(A) and 11(B) illustrate waveform examples of an acceleration detection value in a case where the biological information detection device is attached and detached.
Figure 11B:
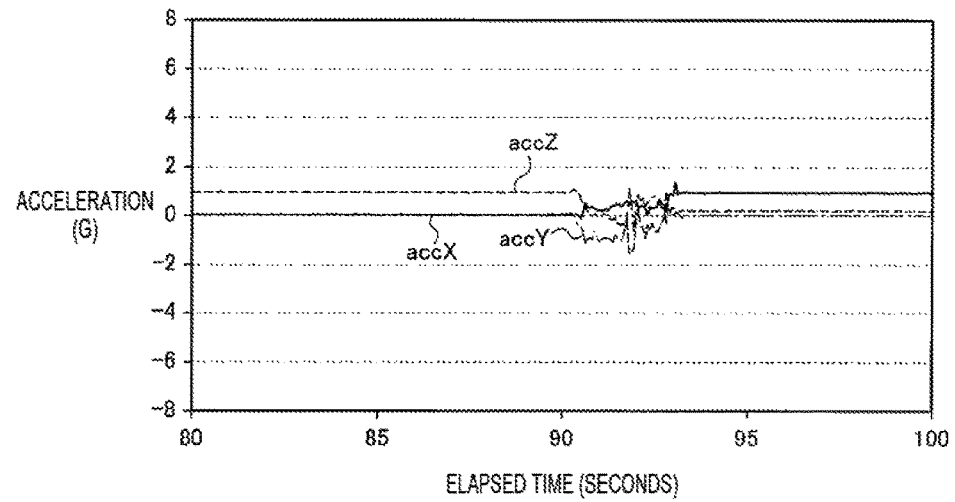

On the other hand, in the same manner as in FIGS. 10(A) and 10(B), FIG. 11(A) illustrates changes in sensor information (acceleration detection value) from the acceleration sensor in a case where the biological information detection device is detached from the arm at the times when 60 seconds, 120 seconds, and 187 seconds elapse, and the biological information detection device is mounted on the arm at the times when 90 seconds, 150 seconds, and 206 seconds elapse. In addition, FIG. 11(B) illustrates that a location around a portion where the elapsed time is 90 seconds is enlarged in order to observe an acceleration change in detail when each of attachment and detachment is performed once. As can be seen from now on, an acceleration detection value becomes about ±1 G at most in a case of the attachment and detachment.

In other words, an acceleration threshold value Thacc satisfying 1 G≤Thacc≤2 G is set, and the absolute maximum value Accmax of the acceleration detection value is compared with Thacc in a period of about one second including the timing at which the DC component changes, so that an impact detection can be performed. Specifically, if Accmax>Thacc, it may be determined that an impact is detected, and if Accmax≤Thacc, it may be determined that an impact does not occur.

In other words, when combined with a determination using ΔDC1 in the period T1, if ΔDC1>Th1 and Accmax≤Thacc, it is determined the biological information detection device is detached, and if ΔDC1>Th1 and Accmax>Thacc, it is determined that detachment is not performed but an impact is applied.

Figure 9A:
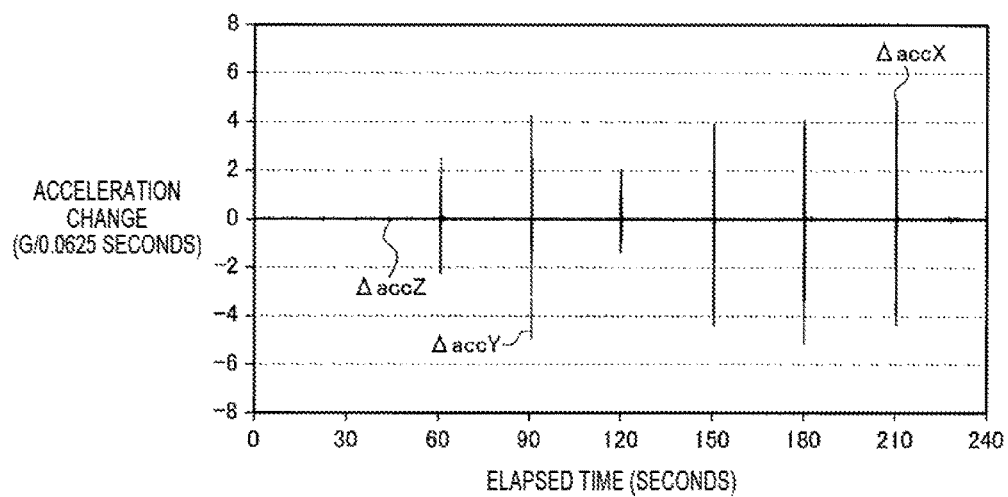
FIGS. 9(A) and 9(B) illustrate waveform examples of a differential value of an acceleration detection value in a case where an impact is applied.
Figure 9B:
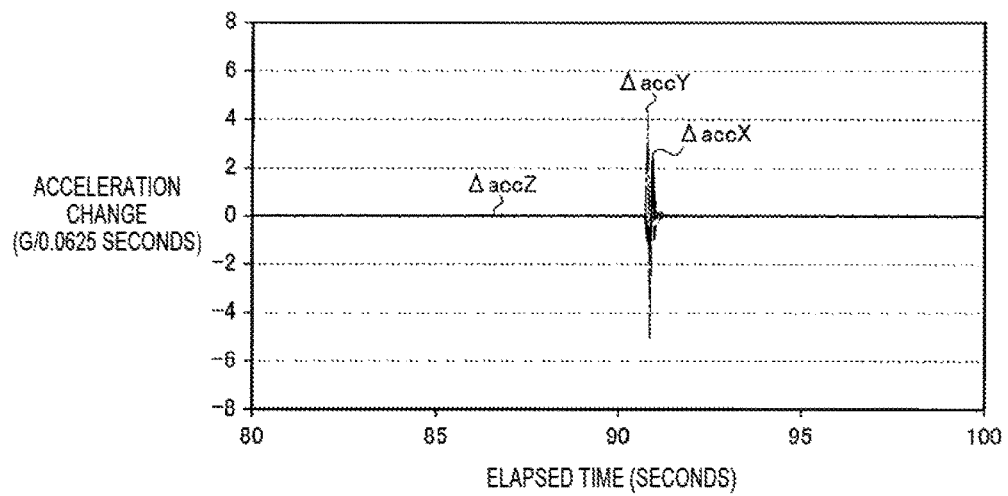
Figure 12A:
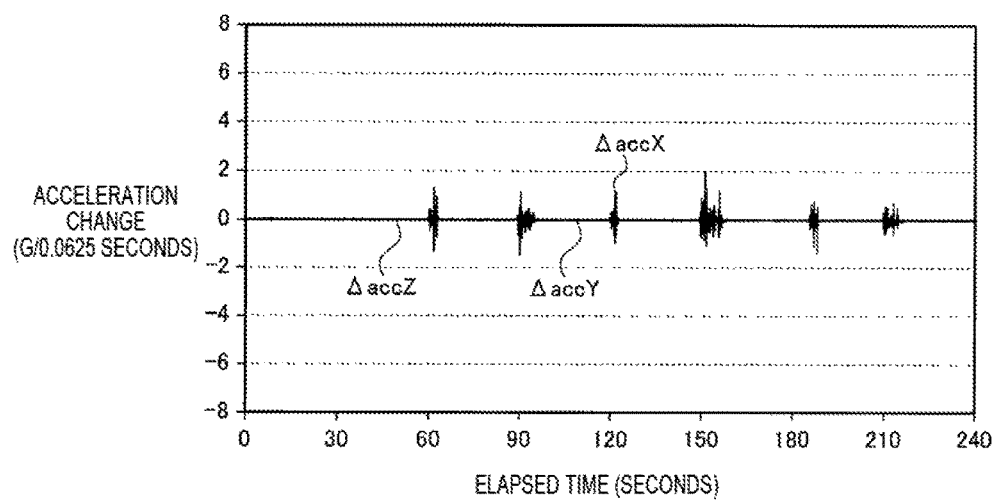
FIGS. 12(A) and 12(B) illustrate waveform examples of a differential value of an acceleration detection value in a case where the biological information detection device is attached and detached.
Figure 12B:
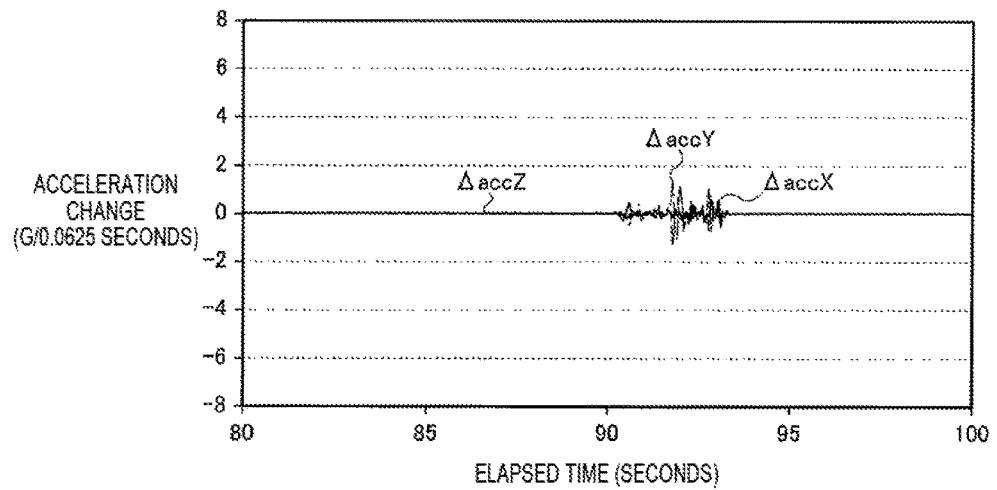

In addition, as can be seen from an acceleration detection value accZ on the Z axis in FIGS. 8(B) and 11(B), if the acceleration detection value itself is used, the determination is influenced by the gravitational acceleration superimposed on an acceleration signal. Therefore, in order to increase accuracy of the impact determination using the acceleration detection value, a process may be performed by using a discrete differential value of the acceleration detection value instead of the acceleration detection value itself. For example, as the discrete differential value, a difference value between the acceleration detection values which are temporally adjacent to each other may be used, and FIG. 9(A) illustrates discrete differential values corresponding to FIG. 8(A). Similarly, FIG. 9(B) illustrates discrete differential values corresponding to FIG. 8(B), FIG. 12(A) illustrates discrete differential values corresponding to FIG. 11(A), and FIG. 12(B) illustrates discrete differential values corresponding to FIG. 11(B). As can be seen from comparison between FIG. 9(B) and FIG. 12(B), a case of taking the discrete differential value also has a similar result in that Accmax (strictly, ΔAccmax) is a greater value when an impact is applied than when detachment or the like is performed. In addition, since the gravitational acceleration is canceled by performing differentiation, a determination can be performed with higher accuracy than in a case of using the acceleration detection value itself.

In addition, a method of minimizing an influence of the gravitational acceleration is not limited to taking a discrete differential value. For example, a high-pass filter process may be performed on a signal with the acceleration detection value in FIG. 8(A), 11(A), or the like, and a comparison process with Thacc may be performed.

3.3 Method Using Autocorrelation Function of AC Component

In addition, in the present embodiment, a mounted state or an unmounted state may be determined by using an autocorrelation function of an AC component signal of a pulse wave sensor signal along with the above-described methods.

An AC component of a pulse wave sensor signal in a mounted state shows a signal corresponding to a user's pulse, and thus shows a signal having periodicity. In addition, in a case where a user wearing the biological information detection device is exercising, there is a possibility that a signal value caused by the exercise is superimposed on the AC component, but there are a lot of exercise having periodicity, such as walking, and thus an AC component signal also has periodicity.

In contrast, it is unlikely that there is a factor which causes an AC component to have periodicity in an unmounted state, and, generally, an AC component signal is a signal having no periodicity.

The autocorrelation function is a function given by the following Equation (1). Here, N is a target section, and may be, for example, 64 samples (a section corresponding to four seconds at a sampling frequency of 16 Hz).

[Equation 1] (1)

$$R(j) = \frac{1}{N}\sum_{i=1}^{N} p(i)p(i-j)$$

$$j = 1, 2, 3, \cdots N$$

In other words, R(j) is a single correlation coefficient between a signal of a focused section and a signal of a section which is j samples earlier than the focused section. The autocorrelation function is obtained by calculating R(j) at j=1 to N.

Figure 13A:
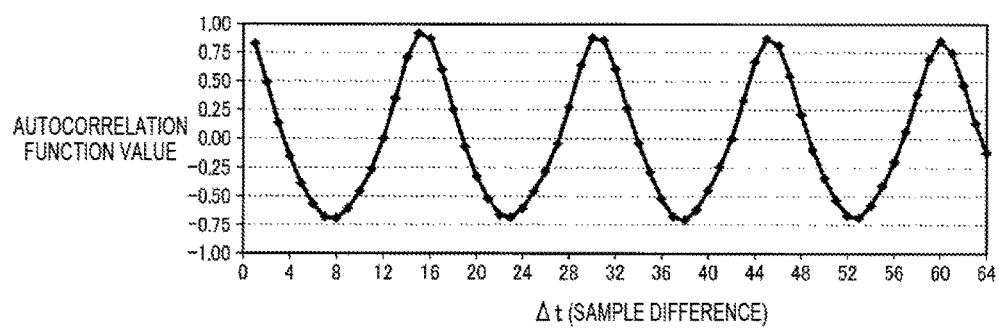
FIGS. 13(A) and 13(B) illustrate examples of an autocorrelation function of the AC component in a mounted state and an unmounted state.
Figure 13B:
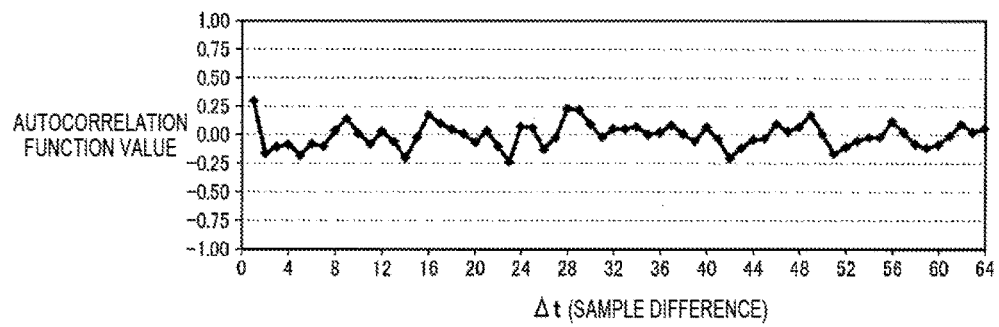

FIGS. 13(A) and 13(B) illustrate examples of a correlation function which is calculated by using the above Equation (1) and the values of the AC component illustrated in FIG. 10(A). FIG. 13(A) illustrates a correlation function in a mounted state (90 seconds to 120 seconds, and the like in FIG. 10(A)), and FIG. 13(B) illustrates a correlation function in an unmounted state (60 seconds to 90 seconds, and the like in FIG. 10(A)).

As can be seen from FIG. 13(A), the autocorrelation function in the mounted state has a great maximum value and a small minimum value. Specifically, a range of the values exceeds ±0.75. Further, the autocorrelation function has periodicity. On the other hand, as can be seen from FIG. 13(B), in the unmounted state, a range of the autocorrelation function is narrow, and the autocorrelation function does not have periodicity. This is because, as described above, there is a high possibility that an AC component has periodicity in the mounted state, but, in contrast, the AC component does not have periodicity in the unmounted state.

Therefore, an autocorrelation function of an AC component of a pulse wave sensor signal is obtained, and it is possible to determine whether or not the biological information detection device is in a mounted state on the basis of the autocorrelation function. Specifically, if the maximum value of the autocorrelation function exceeds ±0.75, the autocorrelation function has periodicity, or both of the two are satisfied, it may be determined that the biological information detection device is in a mounted state. In addition, whether or not the autocorrelation function has periodicity may be determined by performing frequency analysis such as FFT.

4. State Transition

In the present embodiment, a process of determining whether the biological information detection device is in a mounted state or an unmounted state is performed by using a state machine in which an output and the next state are specified on the basis of the current state and an input. In addition, not only the mounted state and the unmounted state but also an intermediate state indicating a middle therebetween is set. Hereinafter, a description will be made of setting of a state and setting of an event indicating an input in each state, and details thereof will be described by using state charts and flowcharts.

4.1 Setting of State and Event

FIG. 14 illustrates examples of states set in the present embodiment and events corresponding to inputs in the respective states. As illustrated in FIG. 14, in the present embodiment, a pulse measurement unsuccessful state, a mounted state (reliable), a mounted state (doubtful), an unmounted state (reliable), an unmounted state (doubtful), a measurement finish state are set. However, states and events in the present embodiment are not limited to the states and events illustrated in FIG. 14, and may be variously modified.

The pulse measurement unsuccessful state (hereinafter, referred to as a state A) is a state in which measurement is started by pressing a measurement start button or the like, but measurement of pulse wave information (pulse rate) is not successful.

The mounted state (reliable) (hereinafter, referred to as a state B) is a state in which the biological information detection device is reliably mounted, and display or the like of pulse wave information is normally performed. The mounted state (doubtful) (hereinafter, referred to as a state C) is a state in which abnormality is observed in a DC component of a pulse wave sensor signal, but the biological information detection device is mounted. The mounted state (doubtful) is included in a mounted state in a broad sense, but corresponds to an intermediate state as the middle between the mounted state and the unmounted state in the meaning that a signal which cannot be observed in a normal mounted state is detected.

The unmounted state (reliable) (hereinafter, referred to as a state D) is a state in which the biological information detection device is reliably detached. The unmounted state (doubtful) (hereinafter, referred to as a state E) is a state in which there is a possibility of mounting of the biological information detection device but detection of pulse wave information is not successful. The unmounted state (doubtful) is not the same as the mounted state (reliable) in that there is a possibility of mounting but pulse wave information or the like cannot be displayed. In other words, the unmounted state (doubtful) also corresponds to an intermediate state as the middle between the unmounted state and the mounted state.

The measurement finish state (hereinafter, referred to as a state F) is a state in which the unmounted state lasts for a long period of time and thus measurement is regarded to be finished.

In addition, an event to be monitored in each state is set in each of the state A to the state E. In each state, if an event does not occur, the state lasts, and if a certain event occurs, a process corresponding to the event is performed (outputting is performed), and the state transitions to another state.

In the state A, the occurrence of an initial pulse measurement successful event (event A1) and an unsuccessful measurement lasting event for specific time (event A2) is monitored. The event A1 is an event which is detected when measurement of pulse wave information (pulse) is successful after transition to the state A. On the other hand, the event A2 is an event which is detected when a specific time elapses without the occurrence of the event A1 after transition to the state A.

In the state B, the occurrence of a detachment event (event B1) and an impact occurrence event (B2) is monitored. The event B1 is an event which is detected when detachment is performed, and, specifically, occurs when $\Delta DC1$ is greater than Th1 and an impact is not detected, as described above. In addition, the event B2 is an event which is detected when an impact occurs, and, specifically, occurs when $\Delta DC1$ is greater than Th1 but an impact is detected.

In the event C, the occurrence of a detachment event (event C1) and an impact end event (event C2) is monitored. The event C1 is an event which is detected when detachment is performed in the same manner as the event B1. C1 may be detected in the exactly same process as in B1, and the threshold values (Th1, Th2, Thacc, and the like) used for determination may be replaced with each other in C1 and B1. The event C2 is an event which is detected when an impact detected during transition to the state C ends. Specifically, the event C2 may be detected in a condition in which an impact is not detected for a specific period of time or there is no abnormality in a DC component value ($\Delta DC1$ is smaller) after transition to the state C.

In the state D, the occurrence of a mounting detection event (event D1) and an unmounted state lasting event for specific time (event D2) is monitored. The event D1 is detected when a DC component change value $\Delta DC3$ in a predetermined period T3 (which is a period after transition to the state D and is almost the same duration as T1) is greater than a predetermined threshold value Th3. As illustrated in FIG. 10(B), a DC component change value in remounting is smaller than a DC component change value in detachment. Therefore, Th3 is required to be set to a value which is small enough to detect even a relatively small DC component change. This may be realized by setting Th1 (=Th3) as a common value of Th3 and Th1 to a value which is small enough to detect remounting, or may be realized by setting a threshold value satisfying Th1>Th3. In the event D1, in accordance therewith, whether or not a DC component signal value shifts before and after a DC component changes may be used for determination in the same manner as $\Delta DC2$ in the period T2. Alternatively, whether or not a DC component signal value after changing is stabilized may be used for determination, and whether or not a waveform of an AC component of a pulse wave sensor signal is fine may be used for determination. Whether or not a waveform is fine may be determined by using an autocorrelation function as described above.

In addition, the event D2 is an event which is detected when a specific time elapses without the occurrence of the event D1 after transition to the state D.

In the state E, the occurrence of an external light detection event (event E1) and a middle pulse measurement successful event (event E2) is monitored. The event E1 is an event which occurs when external light is detected, and, specifically, occurs when a DC component value of a pulse wave sensor signal is a value corresponding to light intensity which is not expected in a mounted state. The event E2 occurs when mounting is detected in the state D, and then further measurement of pulse wave information is successful after transition to the state E. Specifically, the event E2 occurs when further measurement of pulse wave information is successful in conditions in which there is no abnormality in a DC component ($\Delta DC1$ is smaller), a DC component signal value is within some numerical value range, and a waveform of an AC component is fine.

4.2 State Chart

Figure 15:
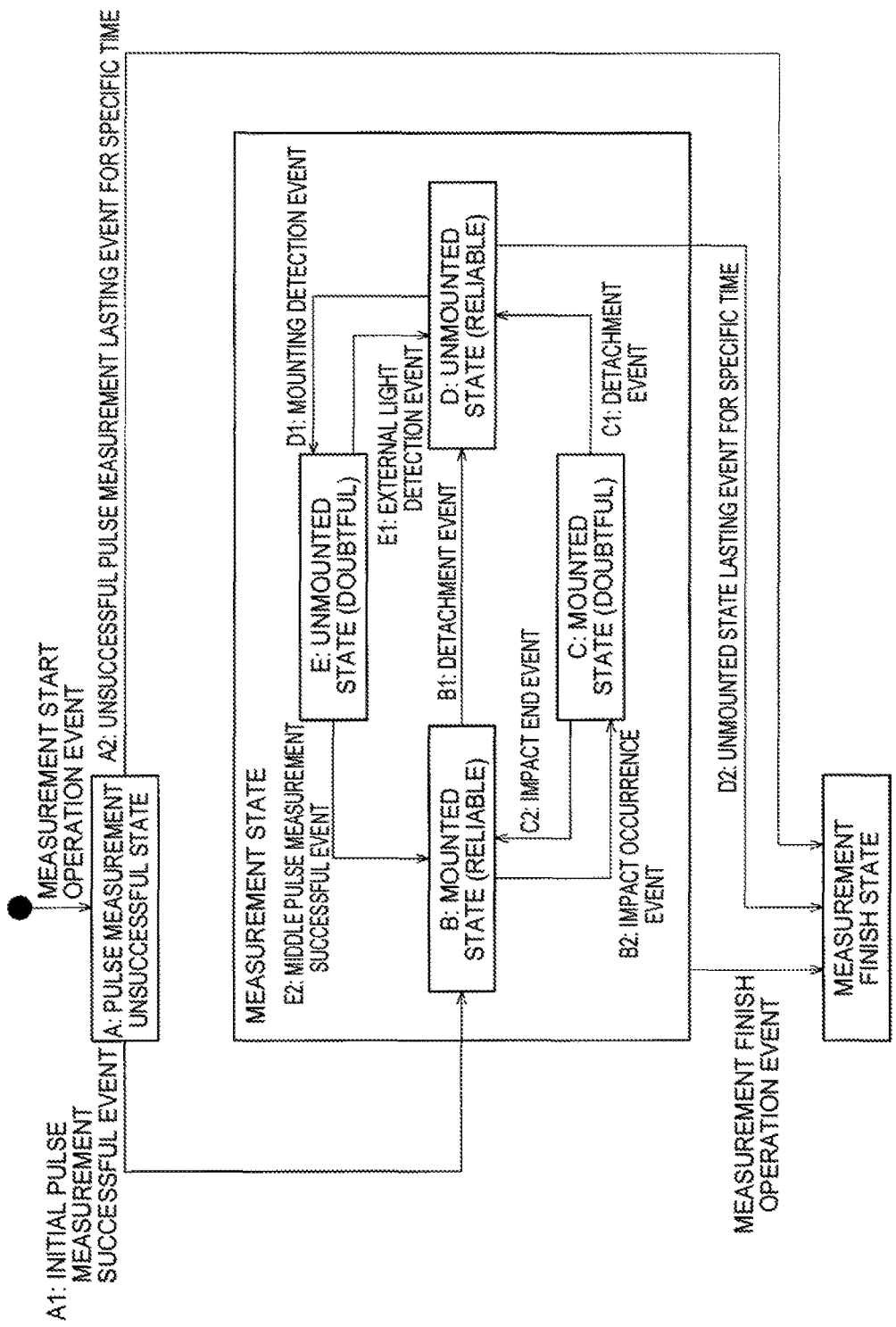
FIG. 15 illustrates an example of a state chart.

FIG. 15 illustrates a state chart of the present embodiment. As illustrated in FIG. 15, first, transition to the state A occurs due to a measurement starting operation event. In the state A, if the event A1 occurs, transition to the state B occurs, and if the event A2 occurs, transition to the state F occurs.

In the state B, if the event B1 occurs, transition to the state D occurs, and if the event B2 occurs, transition to the state C occurs.

In the state C, if the event C1 occurs, transition to the state D occurs, and if the event C2 occurs, transition to the state B occurs.

In the state D, if the event D1 occurs, transition to the state E occurs, and if the event D2 occurs, transition to the state F occurs.

In the state E, if the event E1 occurs, transition to the state D occurs, and if the event E2 occurs, transition to the state B occurs.

The state B to the state E correspond to states during measurement, and transition occurs therebetween until the measurement is finished. In addition, the state B corresponds to a mounted state, the state D corresponds to an unmounted state, and the state C and the state E correspond to intermediate states. However, when taking into consideration the fact that pulse wave information is displayed in the state C, and measurement of pulse wave information is not successful and is not displayed in the state E, the state C is a state close to a mounted state in a broad sense, and the state E is a state close to an unmounted state in a broad sense.

As can be seen from FIG. 15, transition from a mounted state to an unmounted state (from the state B to the state D) may be performed via an intermediate state (the state C), and may be directly performed. This is because there is no occurrence of problems in storage, display, or the like of pulse wave information even if direct transition from the mounted state to the unmounted state is performed. In contrast, transition from the unmounted state to the mounted state is required to be performed via an intermediate state (the state E). This is because appropriate pulse wave information cannot be promptly measured even if the biological information detection device is mounted, and there is a concern that an inappropriate signal is falsely recognized as a signal originating from a pulse if direct transition from the unmounted state to the mounted state is performed.

4.3 Details of Process

Figure 16:
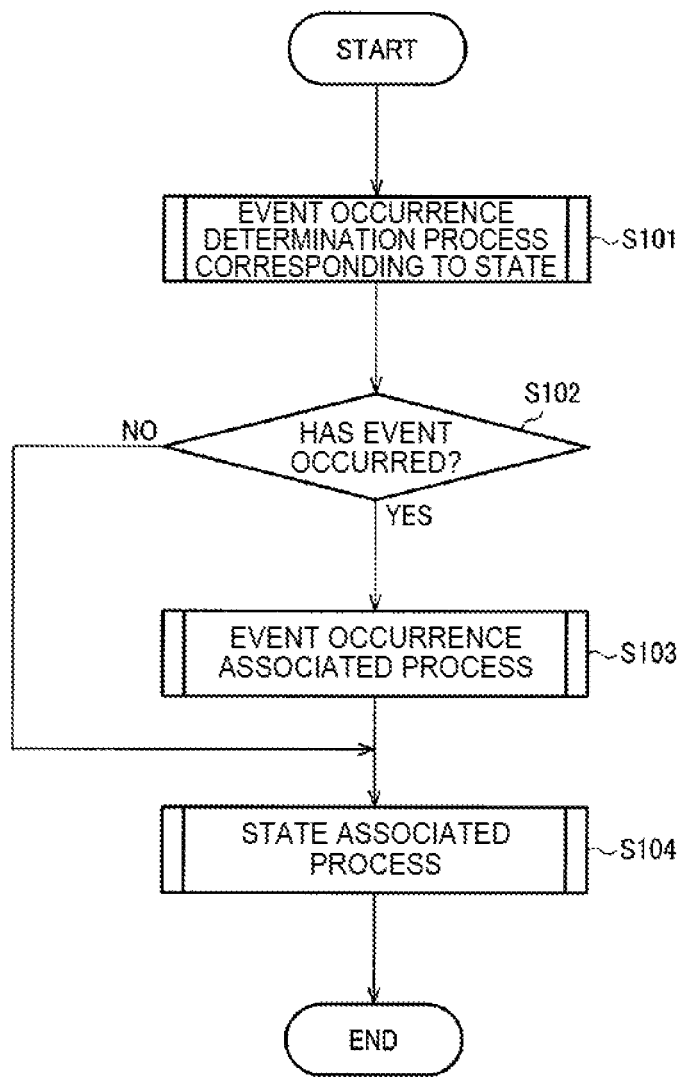
FIG. 16 is a flowchart illustrating a fundamental process in the present embodiment.
Figure 17:
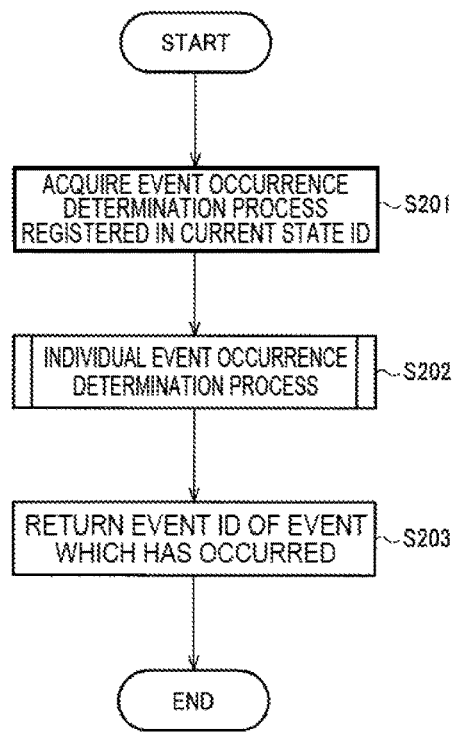
FIG. 17 is a flowchart illustrating an event occurrence determination process.

A description will be made of a flow of a process of the present embodiment by using a flowchart or the like. FIG. 16 illustrates a flow of a fundamental process of the present embodiment. If the process is started, first, an event occurrence process corresponding to the current state is performed (step S101). FIG. 17 illustrates details of the process in step S101. In the process in step S101, first, an event occurrence determination process registered in a current state ID is acquired (step S201). For example, if the current state is the state A, a determination process of each of the event A1 and the event A2 is acquired. Specifically, there may make acquisition of information indicating that the event A1 is determined on the basis of a determination of whether or not pulse wave information has been measured, and information indicating that the event A2 is determined on the basis of a determination of whether or not the state A lasts for a specific period of time. In addition, a process of determining whether or not an event has actually occurred on the basis of the information acquired in step S201 (step S202). Further, if it is determined that any event has occurred in step S202, an ID of the event is returned (step S203).

After the process in step S101 is performed, it is determined whether or not an event has occurred (step S102). This may be performed by determining whether or not a specific event ID has been returned in step S203. In addition, if any event has occurred, an event occurrence associated process which is a process associated with the event is performed (step S103).

Figure 18:
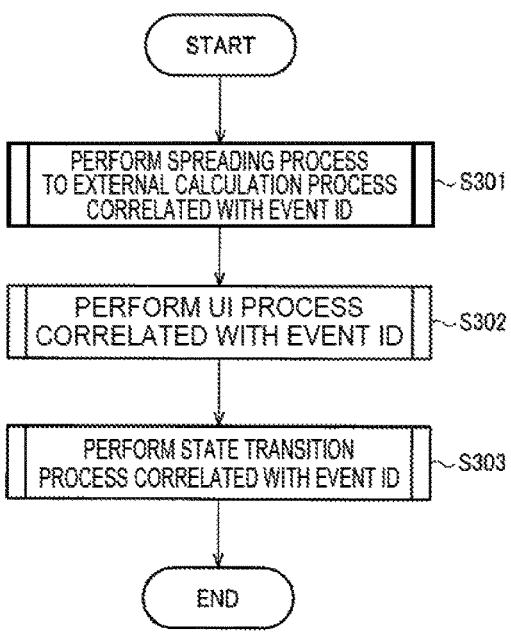
FIG. 18 is a flowchart illustrating an event occurrence associated process.

FIG. 18 illustrates details of the process in step S103. In the event occurrence associated process, a spreading process to an external calculation process correlated with the event ID is performed (step S301), a UI process correlated with the event ID is performed (step S302), and a state transition process correlated with the event ID is performed (step S303). However, an order of steps S301 to S303 is not limited thereto, and the spreading process, the UI process, and the state transition process may be performed in an order which is different from the order in FIG. 18.

The spreading process is to cause a result of attachment or detachment detection to spread to other processes, as in noise filtering or a pulse determination process as illustrated in FIG. 20(A). Specifically, when pulse wave information calculated through a pulse wave information calculation process is stored in the storage unit 300 or is transmitted to other electronic devices via the communication unit 400, a process may be performed in which the pulse wave information is correlated with information indicating that the pulse wave information is acquired in an unmounted state. Alternatively, initialization of a parameter in the pulse wave information calculation process, or initialization (for example, initialization of a filter coefficient) of a noise filter which reduces body movement noise or other noise may be performed.

Figure 21A:
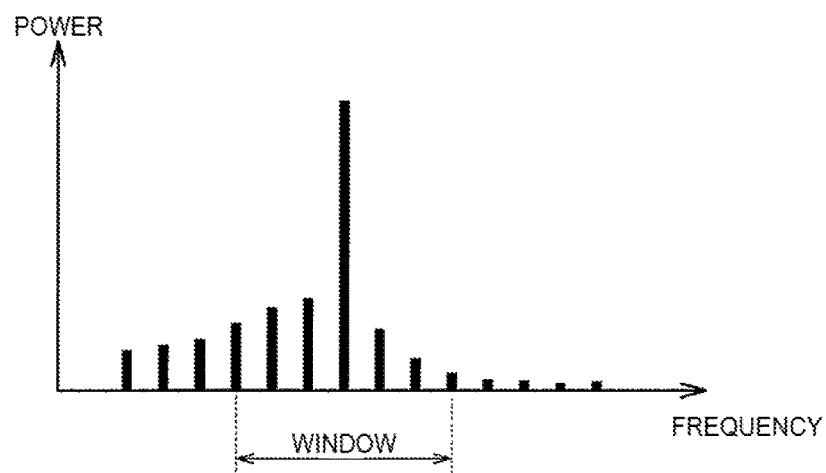
FIGS. 21(A) and 21(B) are diagrams for explaining a parameter in a pulse wave information calculation process.
Figure 21B:
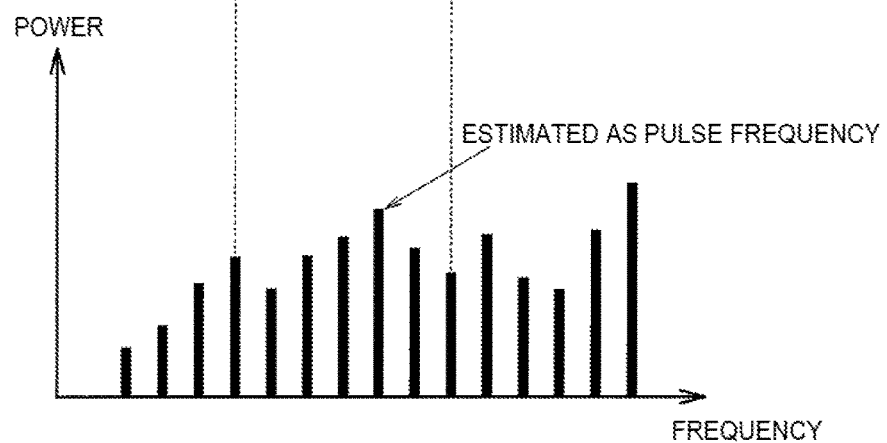

A description will be made of an example of parameter initialization with reference to FIGS. 21(A) and 21(B). The parameter here may be a window indicating a range in which a pulse frequency is estimated to be present when frequency analysis is performed on an AC component of a pulse wave sensor signal. FIGS. 21(A) and 21(B) illustrate examples of results of frequency analysis on an AC component. As illustrated in FIG. 21(A), in a case where a pulse frequency is obtained at a predetermined timing, a window indicating a range of, for example, ±3 of the pulse frequency may be set. In addition, the frequencies which are present in the range of the window are preferentially estimated as the pulse frequencies at the subsequent timings. This is based on the fact that a human pulse frequency does not rapidly change in a short period of time. For example, it is hard to imagine a case where a pulse rate of 60 of a user at a certain timing changes to a pulse rate of 150 at the next timing, and a pulse rate is also expected to be close to 60 at the next timing.

If such a window is set, as illustrated in FIG. 21(B), a pulse frequency can be estimated even in a case where an influence of noise or the like is strong, and a frequency peak cannot be clearly specified. In the example illustrated in FIG. 21(B), a difference between a great power value and a small power value is small, and a frequency of which power is the maximum is present outside the range of the window. Also in such a case, if the window is set on the basis of FIG. 21(A), a plausible frequency can be estimated as a pulse frequency.

However, such a window is a parameter used to estimate a certain peak even in a case where a peak is not clear. As a result, even in a case where the biological information detection device is in an unmounted state, and a signal originating from a pulse is not actually acquired, a peak is forced to be estimated due to an effect of the window, and thus there is a possibility of false recognition that a pulse frequency is obtained. Therefore, in the present embodiment, in a case where an event directed toward transition to an unmounted state occurs, the window may be initialized. In the above-described way, a failure or the like in measurement of pulse wave information can be output without estimating a pulse frequency by force in the case illustrated in FIG. 21(B).

In addition, in the present embodiment, an adaptive enhancer (an adaptive filter in a broad sense) may be used to reduce body movement noise included in a pulse wave sensor signal or other various types of noise. In the adaptive enhancer, in a process of separating a measured signal value into a target signal and a noise signal having periodicity, the noise signal is predicted by using linear integration of past samples. In other words, a filter coefficient of an adaptive filter which is the adaptive enhancer is specified on the basis of the past signal value.

When the filter coefficient is specified, a signal in which noise is superimposed on a signal originating from a pulse is required to be used as the measured signal value. However, in an unmounted state, a signal originating from a pulse is not acquired in the first place, and the measured signal value also includes a signal which is not expected in a mounted state, such as external light. In other words, if learning in the adaptive enhancer is performed by using a measured value in an unmounted state, this causes accuracy of the adaptive enhancer to be reduced. Therefore, in the present embodiment, the adaptive enhancer may be initialized (a filter coefficient of the adaptive filter is initialized in a narrow sense) in a situation corresponding to an unmounted state. In addition, since a filter coefficient which is acquired on the basis of information in the unmounted state is preferably initialized, the initialization process is not required to be performed in the unmounted state at all times. For example, the initialization process may be performed for each predetermined period, and the initialization process may be performed at a timing at which remounting is detected after detachment is detected (a timing at which transition from the state D to the state E occurs in a narrow sense).

In addition, a process related to the adaptive enhancer is not limited to the initialization process of a filter coefficient in a case where detachment of the biological information detection device is detected. For example, in a case where detachment of the biological information detection device is detected through a detachment detection process, the processing unit 100 may stop an adaptive process in the adaptive enhancer which is applied to a pulse wave sensor signal.

As described above, if learning (adaptive process) in the adaptive enhancer is performed by using information in the unmounted state, there is a concern that accuracy of the adaptive enhancer may be reduced. In other words, if learning in the unmounted state can be avoided, accuracy of the adaptive enhancer can be prevented from being reduced, and thus the initialization process of a filter coefficient is not necessarily required to be performed. Specifically, in a case where detachment of the biological information detection device is detected, learning may be temporarily stopped. In addition, learning may be resumed in a case where a predetermined period has elapsed, or in a case where remounting of the biological information detection device is detected (in a case where transition from the state D to the state E occurs in a narrow sense). Further, the filter coefficient initialization process and the learning stopping process are not limited to performing either one thereof, and may be modified, such as performing the filter coefficient initialization process when learning is resumed after the stopping process is performed.

In addition, the UI process is a process or the like of notifying a user that a predetermined event has occurred, by using a "screen", "sound", and "vibration" as illustrated in FIG. 20(A). Further, the UI process is not limited to screen display or generation of sound or vibration, and includes all processes which act on a user's perception as a result, such as notifications using light or transmission of data to other electronic devices.

The state transition process is a process of causing the current state to other states by using the state chart as described above.

Figure 19:
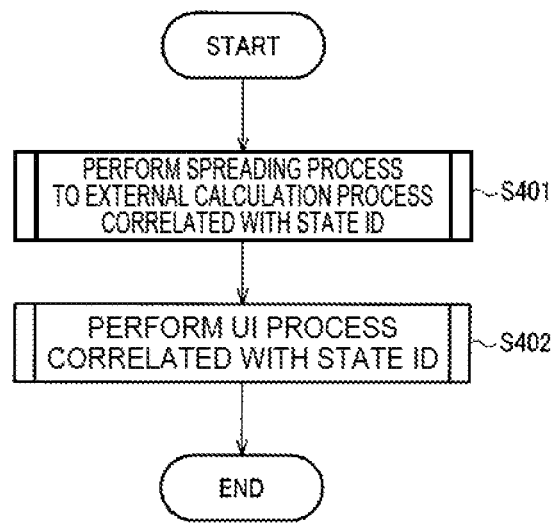
FIG. 19 is a flowchart illustrating a state associated process.

If No in step S102, or after the process in step S103 is performed, a state associated process is performed (step S104). In other words, if No in step S102, state transition does not occur, and thus a process associated with an original state is performed. If Yes in step S102, and the process in step S103 is performed, a process associated with the previous state which has undergone the transition in the state transition process in step S303. FIG. 19 illustrates details of the process in step S303. In the state associated process, a spreading process to an external calculation process correlated with the state ID is performed (step S401), and a UI process correlated with the state ID is performed (step S402). The spreading process and the UI process are the same as those in the event occurrence associated process. In addition, specific examples of the spreading process and the UI process in the state associated process are illustrated in FIG. 20(B). Further, in the spreading process, a parameter initialization process in the above-described pulse wave information calculation process or a filter coefficient initialization process may be performed. Particularly, such a process is preferably performed in an unmounted state and thus may be performed not as the event occurrence associated process but as the state associated process corresponding to an unmounted state (including not only the state D but also the state E).

In the process according to the present embodiment, the flow of the fundamental process illustrated in FIG. 16 is periodically executed. In addition, in the example illustrated in FIG. 16, the event occurrence associated process is performed only when an event occurs, and the state associated process is performed whenever the fundamental process flow is executed, but the present embodiment is not limited thereto. For example, the state associated process may also be performed only when an event occurs (in a case where state transition occurs in a narrow sense).

5. Specific Examples of Present Embodiment

In the above-described present embodiment, the biological information detection device includes, as illustrated in FIG. 3, the pulse wave detection unit 10 which outputs a pulse wave sensor signal, and the processing unit 100 which processes the pulse wave sensor signal. In addition, the processing unit 100 performs a detachment detection process of the biological information detection device on the basis of a DC component change value of the pulse wave sensor signal in a predetermined period. Further, as illustrated in FIG. 3, the pulse wave detection unit 10 may include the pulse wave sensor 11.

Consequently, it is possible to detect detachment of the biological information detection device on the basis of the DC component change value (specifically, $\Delta DC1$ described above) of the pulse wave sensor signal in the predetermined period (specifically, the period T1). As disclosed in PTL 1, it is known that a DC component signal value differs in a mounted state and an unmounted state, but the DC component signal value changes due to various factors. For this reason, it is difficult to set a threshold value for clearly discriminating a signal value in a mounted state from a signal value in an unmounted state in various situations. In relation to this fact, if a DC component change value is used, the change due to the various factors is added to signal values before and after the change, and thus it is possible to perform attachment or detachment detection with high accuracy by minimizing influences of the various factors.

FIGS. 22(A) to 22(C) illustrate evaluation results of the method of the present embodiment. FIGS. 22(A) to 22(C) illustrate examples of various signal values in a case where the biological information detection device is in a mounted state for the elapsed time of 0 seconds to 60 seconds, an operation of grasping and shaking the biological information detection device is performed as an unmounted state from 60 seconds to 120 seconds, and then an operation of remounting the biological information detection device is performed after 120 seconds. FIG. 22(A) is a diagram illustrating an AC component and a DC component of a pulse wave sensor signal, and FIG. 22(B) is a diagram illustrating a DC component change value $\Delta nC1$. In addition, FIG. 22(C) is a diagram illustrating comparison of a change in a pulse rate measured in this situation between the method of the related art and the method of the present embodiment.

In the method of the related art, as described above, since there is a problem in accuracy of detachment detection, an unmounted state occurs after 60 seconds have elapsed, detachment cannot be detected despite an appropriate pulse rate not being acquired, and a certain pulse rate is estimated and is output. This is because, as described above with reference to FIGS. 21(A) and 21(B), a parameter (window) which causes a certain value to be easily estimated is set even if a level of noise or the like is high. In addition, an abnormal pulse rate is output from around 130 seconds to 170 seconds. This is estimated to be influenced by a change in the pulse wave sensor signal due to remounting performed when 120 seconds elapse.

In contrast, in the method of the present embodiment, as illustrated in the timings at which 60 seconds and 120 seconds elapse in FIG. 22(B), the process is performed by using a DC component change value in detachment (and remounting) showing a remarkable value compared with that at normal times, and thus it is possible to detect detachment with high accuracy. Specifically, as illustrated in FIG. 22(C), a pulse rate is 0 (measurement is not possible) in the detachment period after 60 seconds have elapsed.

In addition, if a determination is to be performed with high accuracy in the method of the related art, it is necessary to use a method in which detection of detachment is defined when a plurality of detection determinations are performed, or a method in which detection of detachment is defined when a plurality of detection determination are performed by using multiple methods. For this reason, in most cases, there is a time lag after an actual detachment process is performed until detachment of the biological information detection device is detected. In contrast, in the method of the present embodiment, as illustrated in FIG. 22(C), detachment can be detected in a short period of time. In the example illustrated in FIG. 22(C), detachment has already been detected at the next process timing after 60 seconds. In addition, in FIG. 22(C), some time is taken after remounting is performed when 120 seconds elapse until a pulse rate can be measured. This is a time lag for accumulating pulse wave sensor signals which are required to calculate pulse wave information. Detection can be performed in a short period of time at timings at which an appropriate pulse waveform can be obtained as a result of the remounting.

In addition, the processing unit 100 may perform the detachment detection process on the basis of a DC component change value of the pulse wave sensor signal in a predetermined period, and a second change value indicating a DC component change of the pulse wave sensor signal in a second period which includes the predetermined period and is longer than the predetermined period.

Here, the second period corresponds to the period T2 illustrated in FIGS. 6(A), 6(B), and the like, and is a period including stable periods before and after a DC component signal value in the predetermined period T1 changes in a narrow sense. In addition, the second change value which is a change value in the second period is, specifically, a difference value between a DC component value at a first timing included in the period T2 and a DC component value at a second timing included in the period T2, as illustrated in FIGS. 6(A) and 6(B). More specifically, the second change value is a difference value between the DC component value at the first timing which is a timing included in a stable state (stable period) of a DC component before the period T1 and the DC component value at the second timing which is a timing included in a stable state of the DC component after the period T1.

Consequently, it is possible to perform the detachment detection process by using not only the DC component change value ΔDC1 in the period T1 which is a relatively short period but also the DC component change value ΔDC2 in the period T2 which includes the period T1 and is longer than the period T1. As illustrated in FIGS. 6(A) and 6(B), in a case where the biological information detection device is actually detached and in a case where the biological information detection device temporarily floats from the skin due to an applied impact, ΔDC1 becomes a fairly great value in both the cases, but values of ΔDC2 are greatly different from each other. Therefore, it is possible to minimize a possibility that temporary floating due to an impact may be falsely detected as detachment and thus to perform the detachment detection process with higher accuracy.

In addition, the processing unit 100 may determine that the biological information detection device is detached in a case where a DC component change value of the pulse wave sensor signal in a predetermined period exceeds a predetermined threshold value, and a second change value in a second period exceeds a second threshold value.

Consequently, it is possible to perform the detachment detection process by performing a comparison process between ΔDC2 and the second threshold value Th2 in addition to a comparison process between ΔDC1 and Th1. As illustrated in FIGS. 6(A) and 6(B), in a case where an impact is applied, ΔDC2 becomes a value close to 0, whereas, in a case where detachment is performed, ΔDC2 becomes a fairly great value. Therefore, if ΔDC1>Th1, and ΔDC2≤Th2, it may be determined that an impact is applied, and ΔDC1>Th1, and ΔDC2>Th2, it may be determined that detachment is performed.

In addition, as illustrated in FIG. 3, the biological information detection device may further include the body movement sensor 21 which outputs a body movement signal. Further, the processing unit 100 determines that the biological information detection device is detached in a case where a DC component change value of the pulse wave sensor signal in a predetermined period exceeds a predetermined threshold value, and a body movement signal in a period corresponding to the predetermined period is equal to or smaller than a predetermined body movement threshold value.

Consequently, it is possible to determine whether or not a change in a DC component signal value is caused by actual detachment, and whether or not the change is caused by floating or deviation of the biological information detection device due to an impact, by using a body movement signal. Specifically, as can be seen from comparison between FIG. 8(B) and FIG. 11(B), an acceleration signal change is about ±1 G at most in a case where detachment is performed, but is about ±2 G to ±4 G in a case where an impact is applied. An impact determination may be performed on the basis of a difference between the acceleration detection values. Specifically, it is determined that an impact is not applied in a case where the acceleration detection value (the maximum value thereof in a narrow sense) Accmax is equal to or smaller than the acceleration threshold value Thacc. In other words, if ΔDC1>Th1, and Accmax<Thacc, it may be determined that detachment is performed. Further, as described with reference to FIGS. 9(B) and 12(B), a determination may be performed by using not a body movement signal (an acceleration detection value in a narrow sense) itself but a change value of the body movement signal.

In addition, in a case where detachment of the biological information detection device is detected through the detachment detection process, the processing unit 100 may perform an initialization process of a parameter in a pulse wave determination process based on a pulse wave sensor signal.

Specifically, the processing unit 100 may perform a process of setting a window corresponding to a predetermined frequency range including a frequency which is determined as a pulse frequency in the past pulse wave determination process, and of preferentially determining a frequency included in the window as a pulse frequency, as the pulse wave determination process based on a pulse wave sensor signal. The processing unit 100 may perform an initialization process of the window in a case where detachment of the biological information detection device is detected through the detachment detection process.

Consequently, in a case where detachment is detected, that is, the biological information detection device is in an unmounted state, it is possible to perform an initialization process of a parameter in the pulse wave determination process. The parameter here may be, for example, the window described with reference to FIGS. 21(A) and 21(B). The window can cause a pulse frequency to be estimated even in a case where there is a lot of noise and thus it is hard to specify a peak frequency of an AC component as in FIG. 21(B). Therefore, if the window is continuously used even in an unmounted state, there is a case where a certain pulse frequency is obtained despite a signal originating from a pulse not being acquired, and thus this is not desirable. In the present embodiment, a parameter is initialized in an unmounted state, and thus an inappropriate pulse frequency is prevented from being estimated in the unmounted state.

In addition, in a case where detachment of the biological information detection device is detected through the detachment detection process, the processing unit 100 may perform an initialization process of a filter coefficient of an adaptive enhancer which is applied to a pulse wave sensor signal.

Consequently, in a case where detachment is detected, that is, the biological information detection device is in an unmounted state, it is possible to perform an initialization process of a filter coefficient of the adaptive enhancer. The adaptive enhancer separates a noise signal so as to obtain a signal originating from a pulse under the assumption that the signal originating from a pulse and the noise signal are superimposed on a measured signal. In other words, if learning of a filter coefficient of the adaptive enhancer is performed in the unmounted state, a measured signal which does not include a pulse signal is used, and thus accuracy (for example, accuracy of noise reduction) of the adaptive enhancer is reduced. In the present embodiment, a filter coefficient is initialized in the unmounted state, and thus inappropriate learning in the adaptive enhancer is prevented from being performed in the unmounted state. In addition, since a filter coefficient which is acquired on the basis of information in the unmounted state is preferably initialized, the initialization process is not required to be performed in the unmounted state at all times. For example, the initialization process may be performed for each predetermined period, and the initialization process may be performed at a timing at which remounting is detected after detachment is detected (a timing at which transition from the state D to the state E occurs in a narrow sense).

In addition, a process related to the adaptive enhancer is not limited to the initialization process of a filter coefficient in a case where detachment of the biological information detection device is detected. For example, in a case where detachment of the biological information detection device is detected through a detachment detection process, the processing unit 100 may stop an adaptive process in the adaptive enhancer which is applied to a pulse wave sensor signal.

As described above, if learning (adaptive process) in the adaptive enhancer is performed by using information in the unmounted state, there is a concern that accuracy of the adaptive enhancer may be reduced. In other words, if learning in the unmounted state can be avoided, accuracy of the adaptive enhancer can be prevented from being reduced, and thus the initialization process of a filter coefficient is not necessarily required to be performed. Specifically, in a case where detachment of the biological information detection device is detected, learning may be temporarily stopped. In addition, learning may be resumed in a case where a predetermined period has elapsed, or in a case where remounting of the biological information detection device is detected (in a case where transition from the state D to the state E occurs in a narrow sense). Further, the filter coefficient initialization process and the learning stopping process are not limited to performing either one thereof, and may be modified, such as performing the filter coefficient initialization process when learning is resumed after the stopping process is performed.

In addition, the processing unit 100 may obtain a difference value between an i-th DC component value of the pulse wave sensor signal at an i-th (where i is a positive integer) sampling timing and a j-th DC component value of the pulse wave sensor signal at a j-th (where j is an integer satisfying j>i) sampling timing, as the DC component change value, and may perform the detachment detection process on the basis of the obtained DC component change value.

Consequently, as illustrated in FIG. 5(A) or 5(B), it is possible to use a difference value between DC component values at a plurality of sampling timings as the DC component change value $\Delta DC1$ of the pulse wave sensor signal in the predetermined period T1. As illustrated in FIG. 5(A), if a difference value (in a case of j=i+1) at sampling timings which are adjacent to each other is used, it is possible to perform the detachment detection process at a higher speed than in the case illustrated in FIG. 5(B). In addition, as illustrated in FIG. 5(B), if a difference value (in a case of j>i+1) at sampling timings which are not adjacent to each other is used, it is possible to appropriately obtain the change value $\Delta DC1$ even in a case where a DC component signal value relatively smoothly changes, as in a case where a DC component changes over a plurality of sampling timings.

In addition, the processing unit 100 may determine that the biological information detection device is detached in a case where a DC component change value of the pulse wave sensor signal in a predetermined period exceeds a predetermined threshold value.

Consequently, it is possible to detect detachment on the basis of a comparison process between the DC component change value $\Delta DC1$ and the predetermined threshold value Th1. As illustrated in FIG. 4 or the like, $\Delta DC1$ at a timing corresponding to detachment becomes a sufficiently greater value than a value close to 0 at normal times, and thus it may be determined that detachment is performed if $\Delta DC1 > Th1$ by setting the appropriate threshold value Th1.

Further, the processing unit 100 may perform a remounting detection process of the biological information detection device on the basis of a third change value indicating a change in a DC component of the pulse wave sensor signal in a third period which is a period after detachment of the biological information detection device is detected through the detachment detection process.

Consequently, it is possible to detect not only detachment of the biological information detection device but also remounting on the basis of a DC component change value. In addition, in a case where the biological information detection device is left on a desk in an unmounted state, and a person passes around the biological information detection device, there is a possibility that a DC component change value $\Delta DC3$ may increase as a result of some external light being blocked by the person. In this case, there is a concern of a wrong determination that transition to a mounted state occurs despite continuity of the unmounted state. Therefore, in the same manner as in the example of impact detection in the detachment determination, a DC component change value ΔDC4 in a period T4 which includes the period T3 and is longer than the period T3 may be obtained, and remounting may be determined by using both of ΔDC3 and the ΔDC4. Specifically, when predetermined threshold values are assumed to be Th3 and Th4, it is determined that the biological information detection device is remounted if ΔDC3>Th3 and ΔDC4>Th4. This is because, in a case where external light is temporarily blocked by a person or the like, a DC component signal value returns to an original value when the blocking factor is removed, and thus ΔDC4 becomes a value close to 0, whereas a DC component signal value shifts in a case where remounting is performed.

In addition, various modifications may occur, for example, if ΔDC3>Th3, and a waveform of an AC component is fine, it is determined that remounting is performed. Further, the case where a waveform of an AC component is fine corresponds to the case of an autocorrelation function of the AC component as illustrated in FIG. 13(A).

In addition, in the above-described present embodiment, the biological information detection device includes, as illustrated in FIG. 3, the pulse wave detection unit 10 which outputs a pulse wave sensor signal, and the processing unit 100 which processes the pulse wave sensor signal. Further, in a case where detachment of the biological information detection device is detected, the processing unit 100 gives an instruction for stopping recording or communication of pulse wave information based on a pulse wave sensor signal, or an instruction for recording or communication of pulse wave information correlated with information indicating that the pulse wave information is acquired in a detachment period.

Here, the information indicating that the pulse wave information is acquired in the detachment period may be, for example, flag information which uses a single bit in a data structure of the pulse wave information and represents whether or not the biological information detection device is in an unmounted state with 0 and 1 of the bit. However, the information is not limited to information simply indicating whether or not the biological information detection device is in an unmounted state, and may be, for example, information which can cause the state D and the state E illustrated in FIG. 14 to be discriminated from each other, and may be information including associated information such as elapsed time after transition to the corresponding state occurs, or the number of times of transition to the corresponding state.

Consequently, in a case where detachment of the biological information detection device is detected, that is, the biological information detection device is in an unmounted state, recording or communication of pulse wave information can be stopped, or although recording or communication is performed, information indicating that the pulse wave information is acquired in a detachment period can be correlated with the pulse wave information. Therefore, the pulse wave information in the unmounted state may not be used in the first place in a subsequent process using the pulse wave information, or it can be clarified that the pulse wave information is acquired in the unmounted state although the information may be used in the future. Here, the process using the pulse wave information is a process which is performed in the biological information detection device or an external device which is a communication destination, and corresponds to, for example, a process of generating an advice or the like regarding a user's health state based on the pulse wave information. As described above, since a signal originating from a pulse is not included in a pulse wave sensor signal, there is a possibility that calculated pulse wave information may not have an appropriate value and may exert an adverse effect on the process using the pulse wave information. However, in a case where the biological information detection device is mounted for a long period of time (mounted at all times in a narrow sense) and is used to acquire a "life log", a case may sufficiently occur in which the biological information detection device is in an unmounted state even during measurement unlike a pulsimeter or the like of the related art. In relation to this fact, in the method of the present embodiment, pulse wave information in an unmounted state may not be used in the first place, or the next process which considers a possibility of inappropriate pulse wave information can be performed.

In addition, the instruction for stopping recording or communication, or the instruction for recording or communication of pulse wave information correlated with information indicating that the pulse wave information is acquired in the detachment period may be given as, for example, the spreading process in the state associated process or the event occurrence associated process as described above with reference to FIGS. 20(A) and 20(B).

Further, in a case where remounting of the biological information detection device is detected, and a process of measuring pulse wave information is successful, after detachment of the biological information detection device is detected, the processing unit 100 may give an instruction for recording or communication of the pulse wave information.

Consequently, in a case where, in an unmounted state, not only is remounting detected, but a process of measuring pulse wave information is also successful, an instruction can be given for recording or communication of the pulse wave information. Typically, not only a pulse wave sensor signal on the moment but also a pulse wave sensor signal in some period before then is required to measure (calculate) pulse wave information. For example, in a case where a frequency analysis process such as FFT is performed on an AC component of a pulse wave sensor signal, signal values in a sufficient period are naturally necessary in terms of a method of the frequency analysis process. In addition, in a case where the frequency analysis is not performed, a time period from a peak of the AC component to the next peak thereof, a time period between rising edges which are approximate to a rectangular wave of the AC component, or the like is obtained, and the time period is used as a pulse cycle. Also in this case, a signal corresponding to one cycle is necessary, and signals corresponding to a plurality of cycles may be used in order to increase accuracy. In other words, if pulse wave information is obtained from the moment of remounting, and recording or communication of the pulse wave information is performed, a pulse wave sensor signal in an unmounted state is used to calculate pulse wave information, and thus an accurate value cannot be calculated. Therefore, in the present embodiment, recording or communication of pulse wave information is not resumed only due to detection of remounting, and an instruction for recording or communication is given after measurement of the pulse wave information is successful. In addition, whether or not a process of measuring pulse wave information is successful may be determined on the basis of, for example, whether or not obtained pulse wave information has a normal value as a person's pulse rate. If a pulse wave sensor signal in an unmounted state is not used, and FFT or the like is performed by treating a value thereof as 0, a value of obtained pulse wave information lacks in appropriateness. In other words, in a case where the pulse wave information has an appropriate value, it can be said that a pulse wave sensor signal which is a target of FFT or the like is acquired in a mounted state, and obtained pulse wave information is also appropriate information in which an actual pulse is reflected. However, a determination of whether or not a process of measuring pulse wave information is successful is not limited thereto. For example, various modifications may occur, such as it being determined that measurement is successful in a case where a proportion of a pulse wave sensor signal acquired in a mounted state, occupying a pulse wave sensor signal which is a target of FFT or the like, is equal to or greater than a predetermined threshold value.

In addition, the processing unit 100 may set a plurality of states including a mounted state corresponding to a case where the biological information detection device is mounted, an unmounted state corresponding to a case where the biological information detection device is detached, and an intermediate state corresponding to the middle between the mounted state and the unmounted state, and may give an instruction for stopping recording or communication or may give an instruction for recording or communication on the basis of a transition process between the plurality of set states.

Consequently, it is possible to perform the process of the present embodiment by using the state machine illustrated in FIG. 15. In this case, the intermediate state is set, and thus not only the mounted state and the unmounted state but also finer states can be set. For example, as illustrated in FIG. 15, a state (the state C) which is included in the mounted state but cannot be said to be a stable mounted state since an abnormal value is observed in a DC component, or, similarly, a state (the state E) which is included in the unmounted state but cannot be a stable unmounted state may be set as the intermediate state. The state C can be said to have a high possibility of transition to the unmounted state compared with the stable mounted state (the state B), and the state E can be said to have a high possibility of transition to the mounted state compared with the stable unmounted state (the state D). For this reason, since an input (corresponding to an event in FIG. 15 or the like) monitored in the state B and the state C can be replaced with other inputs, or an input monitored in the state D and the state E can be replaced with other inputs, a more flexible process can be performed.

In addition, the processing unit 100 may perform a transition process from the unmounted state to the intermediate state in a case where a mounting detection event is detected in the unmounted state, and may perform a transition process from the intermediate state to the mounted state in a case where a pulse wave information measurement successful event is detected in the intermediate state.

The intermediate state here corresponds to the state E illustrated in FIG. 15.

Consequently, it is possible to perform transition from the above-described unmounted state to the mounted state, that is, transition to the mounted state in a case where not only is remounting detected but a process of measuring pulse wave information is also successful, by using the intermediate state. As described above, a situation in which remounting is detected cannot be said to be a stable unmounted state, and cannot be said either to be a mounted state from the viewpoint of measurement of pulse wave information not being possible. In the present embodiment, the corresponding state is set as the state E which is the intermediate state, and two-stage transition occurs, such as transition from the state D to the state E due to the event D1 (detection of mounting), and transition from the state E to the state B due to the event E2 (successful measurement). Consequently, recording or communication of the pulse wave information is not resumed only due to detection of remounting, and an instruction for recording or communication is given after measurement of the pulse wave information is successful.

In addition, the processing unit 100 may perform a detection process of a detachment event and an impact occurrence event in the mounted state, may determine that the biological information detection device is detached and may perform a transition process from the mounted state to the unmounted state in a case where the detachment event is detected, and may determine detection of an abnormality signal indicating that it is doubtful that the biological information detection device is detached and may perform a transition process from the mounted state to the intermediate state in a case where the impact occurrence event is detected.

Here, the mounted state corresponds to the state B, the unmounted state corresponds to the state D, and the intermediate state corresponds to the state C. In addition, the detachment event corresponds to the event B1, and the impact occurrence event corresponds to the event B2.

Consequently, the occurrence of two events can be monitored in the mounted state, and it is possible to determine whether direct transition from a mounted state to an unmounted state is caused to occur or temporary transition from the mounted state to an intermediate state is caused to occur according to the occurred event. Since there is no problem even if direct transition from the mounted state to the unmounted state is caused to occur unlike in the example of measurement of pulse wave information in a case of transition from the unmounted state to the mounted state, transition from the state B to the state D occurs during the occurrence of the detachment event indicating clear detachment. On the other hand, when the impact occurrence event occurs, it is regarded that detachment is not performed, but abnormality is observed in at least a DC component and thus it is certain that the current state is not a stable mounted state. Therefore, transition to the state C which is different from the state B occurs. In addition, in the state C, the occurrence of events which are different from those in the state B may be monitored. For example, both of the event B1 and the event C1 are detachment events, but content (for example, a value of the threshold value Th1) processed in the event B1 and the event C1 may be changed. Further, in a case where the abnormality of the DC component ends in the state C (in a case where the event C2 occurs), as illustrated in FIG. 15, a stable mounted state is obtained through transition to the state B.

In addition, the above-described present embodiment is applicable to the biological information detection device including the pulse wave detection unit 10 that is provided with the pulse wave sensor 11 which outputs a pulse wave sensor signal, and the processing unit 100 that processes the pulse wave sensor signal, in which the processing unit 100 gives an instruction for stopping display of pulse wave information based on the pulse wave sensor signal or performs a display switching process in a case where detachment of the biological information detection device is detected, and gives an instruction for displaying the pulse wave information in a case where remounting of the biological information detection device is detected and a process of measuring the pulse wave information based on the pulse wave sensor signal is successful after the detachment of the biological information detection device is detected.

Here, the instruction for stopping display is an instruction for not displaying pulse wave information on the display unit, and may be an instruction for stopping screen display in a broad sense. On the other hand, the display switching process is a process of allowing pulse wave information to be displayed but changing certain display compared with a display screen in a mounted state. For example, in FIG. 20(B), as indicated in an "icon display type", the process may be a process of changing a displayed icon between a mounted state (the state B and the state C) and an unmounted state (the state D and the state E). Alternatively, as indicated in a "pulse rate", the process may be a process of changing numerical value display to bar display. As indicated in "sensing sensitivity", the process may be a process of performing a change indicating that sensing sensitivity is reduced. In addition, in relation to the display change of the "pulse rate", a state in which a numerical value of a pulse rate is displayed is changed to a state in which the numerical value thereof is not displayed, and thus this may be regarded to be included in an "instruction for stopping display of pulse wave information".

Consequently, when pulse wave information is displayed on the display unit and is presented to a user, it is possible to specify whether the pulse wave information is acquired in a mounted state or an unmounted state. Since pulse wave information is not displayed, or it can be seen that pulse wave information is information in an unmounted state although displayed, it is possible for a user to perform an appropriate determination using the pulse wave information.

Although the present embodiment has been described in detail, it is easily understood by a person skilled in the art that various modifications may occur without substantially departing from the novel matters and effects of the invention. Therefore, such modification examples are all intended to be included in the scope of the invention. For example, in the specification or the drawings, a terminology which is described at least once along with another terminology which has a broader meaning or the same meaning may be replaced with another terminology in any location of the specification or the drawings. In addition, configurations and operations of the biological information detection device are not limited to those described in the present embodiment and may be variously modified.

REFERENCE SIGNS LIST

10: Pulse wave detection unit
11: Pulse wave sensor
12: LED
13: PD
14: Convex portion
16: A/D converter
20: Body movement detection unit
26: A/D converter
100: Processing unit
110: Attachment/detachment detection portion
120: Pulse wave information calculation portion
200: Display unit
300: Storage unit
400: Communication unit
500: Base section
600: Holding mechanism

What is claimed is:

1. A biological information detection device comprising:
  a pulse sensor configured to be mounted to a user and to output a pulse wave sensor signal; and
  a processor configured to receive the pulse wave sensor signal and perform at least one detachment detection process to determine that the pulse wave sensor is detached from the user, wherein a first detachment detection process of the at least one detachment detection process is on a basis of a first change value of a DC component of the pulse wave sensor signal in a predetermined period and a second change value of the DC component of the pulse wave sensor signal in a second period which includes the predetermined period and is longer than the predetermined period, and
  wherein the processor is further configured to give an instruction for stopping recording or communication of pulse wave information based on the pulse wave sensor signal, to give an instruction for recording or communication of pulse wave information correlated with information indicating that the pulse wave information is acquired in a detachment period, to give an instruction for stopping display of pulse wave information based on the pulse wave sensor signal, or to perform a display switching process in a case where detachment of the biological information detection device is detected.

2. The biological information detection device according to claim 1, wherein the processor is configured to determine that the biological information detection device is detached in a case where the first change value of the DC component of the pulse wave sensor signal in the predetermined period exceeds a predetermined threshold value, and the second change value of the DC component of the pulse wave sensor signal in the second period exceeds a second threshold value.

3. The biological information detection device according to claim 1, further comprising:
  a body movement sensor configured to output a body movement signal,
  wherein the processor is further configured to determine that the biological information detection device is detached in a second detachment detection process of the at least one detachment detection process in a case where the first change value of the DC component of the pulse wave sensor signal in the predetermined period exceeds a predetermined threshold value, and the body movement signal in a period corresponding to the predetermined period is equal to or smaller than a predetermined body movement threshold value.

4. The biological information detection device according to claim 1, wherein the processor is configured to perform an initialization process of a parameter in a pulse wave determination process based on the pulse wave sensor signal in the case where detachment of the biological information detection device is detected through the at least one detachment detection process.

5. The biological information detection device according to claim 1, wherein the processor is further configured to perform a remounting detection process of the biological information detection device on a basis of a third change value indicating a change of the DC component of the pulse wave sensor signal in a third period which is a period after detachment of the biological information detection device is detected through the at least one detachment detection process.

* * * * *